(12) United States Patent
Aramini et al.

(10) Patent No.: US 12,285,396 B2
(45) Date of Patent: Apr. 29, 2025

(54) CO-CRYSTAL OF KETOPROFEN, COMPOSITIONS COMPRISING THE SAME, PROCESS OF PRODUCING THE SAME, AND USES THEREOF

(71) Applicant: DOMPÉ FARMACEUTICI S.P.A., Milan (IT)

(72) Inventors: Andrea Aramini, L'Aquila (IT); Gianluca Bianchini, L'Aquila (IT); Samuele Lillini, Cardito (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 874 days.

(21) Appl. No.: 17/416,627

(22) PCT Filed: Dec. 20, 2019

(86) PCT No.: PCT/EP2019/025464
§ 371 (c)(1),
(2) Date: Jun. 21, 2021

(87) PCT Pub. No.: WO2020/126088
PCT Pub. Date: Jun. 25, 2020

(65) Prior Publication Data
US 2022/0071936 A1 Mar. 10, 2022

(30) Foreign Application Priority Data
Dec. 21, 2018 (EP) ..................................... 18215336

(51) Int. Cl.
*A61K 31/192* (2006.01)
*A61K 47/54* (2017.01)

(52) U.S. Cl.
CPC .......... *A61K 31/192* (2013.01); *A61K 47/542* (2017.08)

(58) Field of Classification Search
CPC ........................ C07B 2200/13; A61K 31/192
See application file for complete search history.

(56) References Cited

U.S. PATENT DOCUMENTS

| | | | |
|---|---|---|---|
| 4,279,926 A | 7/1981 | Bruzzese et al. | |
| 5,808,069 A * | 9/1998 | Bosone | C07D 295/088 562/560 |
| 2007/0292515 A1 | 12/2007 | Schobel et al. | |
| 2008/0311201 A1* | 12/2008 | Der-Yang | A61P 11/02 424/472 |

FOREIGN PATENT DOCUMENTS

| | | | |
|---|---|---|---|
| BE | 882889 | 8/1980 | |
| BE | 882889 A * | 8/1980 | ............. C07C 59/84 |
| CN | 1939893 | 4/2007 | |
| CN | 103524365 | 1/2014 | |
| CN | 104987287 | 10/2015 | |
| EA | 000599 | 2/1998 | |
| GB | 1497044 | 1/1978 | |
| GB | 1497044 A * | 1/1978 | ............. C07C 57/30 |
| IT | TO20120978 A1 * | 5/2014 | ............. C07C 59/84 |
| JP | S59190912 | 10/1984 | |
| RU | 2340334 | 1/2006 | |
| RU | 2437657 | 12/2011 | |
| WO | WO 1997024114 | 7/1997 | |
| WO | WO 2004037242 | 5/2004 | |
| WO | WO-2008077813 A2 * | 7/2008 | ........... A61K 9/0056 |
| WO | WO-2011132167 A1 * | 10/2011 | ............. A61J 3/005 |

OTHER PUBLICATIONS

Selleckchem "L-lysine", 2024, https://www.selleckchem.com/datasheet/l-lysine-S563001-DataSheet.html (accessed Jun. 5, 2024) (Year: 2024).*
Sigma "L-Lysine Product Information", 2024, https://www.sigmaaldrich.com/deepweb/assets/sigmaaldrich/product/documents/334/572/15501pis.pdf (accessed Jun. 5, 2024) (Year: 2024).*
Texas Natural Supply "L-Lysine Powder", 2024, https://www.texasnaturalsupply.com/L-Lysine-Powder-p/llsp-nt.htm (accessed Jun. 5, 2024) (Year: 2024).*
Aitipamula et al. "Polymorphs, Salts, and Cocrystals: What's in a Name?" Crystal Growth & Design 2012, 12, 2147-2152. (Year: 2012).*
Almarsson, Örn, et al., "Crystal engineering of the composition of pharmaceutical phases. Do pharmaceutical co-crystals represent a new path to improved medicines?", Chem. Commun., 2004, pp. 1889-1896.
Chen, Shuang, et al., "Chiral co-crystal solid solution: structures, melting point phase diagram, and chiral enrichment of (ibuprofen)2(4,4-dipyridyl)". CRYSTENGCOMM. 12, 2010, pp. 1485-1493.
Kuminek, G. et al., Cocrystals to facilitate delivery of poorly soluble compounds beyond-rule-of-5, Advanced Drug Delivery Reviews, Apr. 29, 2016, vol. 101, pp. 143-166.
English translation of BE882889.

(Continued)

*Primary Examiner* — Bethany P Barham
*Assistant Examiner* — Judith Marie Kamm
(74) *Attorney, Agent, or Firm* — HUESCHEN AND SAGE

(57) ABSTRACT

The present invention relates to a co-crystal of Ketoprofen Lysine named Form 1, characterized by its X-ray powder diffraction diagram, a pharmaceutical composition comprising the co-crystal of Ketoprofen Lysine, a process for the production of the co-crystal of Ketoprofen Lysine, and the use of the co-crystal of Ketoprofen Lysine in the treatment of pain and inflammatory diseases.

14 Claims, 17 Drawing Sheets

(56) References Cited

OTHER PUBLICATIONS

International Search Report for PCT/EP2019/025464 dated Mar. 30, 2020.
Caira, Topics in Current Chemistry, 1998, 198, 164-208.
Duggirala, et al., Chem. Commun., 2016, 52, 640-655.
English translation of Professional Knowledge on Pharmaceutical Areas (I), China Medical Science Press, Jan. 2017, 11th edition, p. 95.
https://www.pharmaexcipients.com/product/eudragit-e-po/, 2024.
Kümmerer, Annu. Rev. Environ. Resour., 2010, 35, 57-75.
Panerai, et al., Trends in Medicine, 2012, 12, 159-167.
Porfiryeva, et al., International Journal of Pharmaceutics, 2019, 562, 241-248.
Professional Knowledge on Pharmaceutical Areas (I), China Medical Science Press, Jan. 2017. 11th edition, p. 95.
Rodriguez-Spong, et al., Advanced Drug Delivery Reviews, 2004, 56, 241-274.
Sarma, et al., Korean J. Chem. Eng., 2011, 28, 315-322.
Variankaval, et al., AlChE, 2008, 54, 1682-1688.
Yadav, et al., Indian Journal of Pharmaceutical Sciences, 2009, Jul.-Aug., 359-370.

\* cited by examiner

CO-CRYSTAL OF KETOPROFEN, COMPOSITIONS COMPRISING THE SAME, PROCESS OF PRODUCING THE SAME, AND USES THEREOF

FIELD OF THE INVENTION

The present invention refers to a co-crystal of Ketoprofen Lysine, a pharmaceutical composition comprising said co-crystal, a process for its production and to its medical use, in particular in the treatment of pain and inflammatory diseases.

BACKGROUND OF THE INVENTION

Ketoprofen, ((RS)-2-(3-benzoylphenyl)-propionic acid, chemical formula $C_{16}H_{14}O_3$) of formula

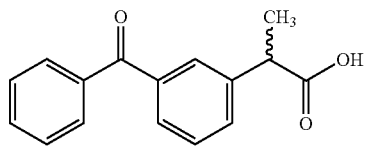 [SMILES: CC(C(=O)O)c1cccc(C(=O)c2ccccc2)c1]

is one of the propionic acid class of nonsteroidal anti-inflammatory drugs (NSAID) with analgesic and antipyretic effects.

Because of its high tolerability, Ketoprofen is one of the non-steroidal anti-inflammatory drugs of widespread use in clinics, both for the treatment of serious inflammatory conditions and for its use in analgesic and antipyretic by inhibiting the body's production of prostaglandin.

Pharmaceutical compositions of current use containing Ketoprofen, have a racemate as its active ingredient, where the two enantiomers S(+) and R(−) are present in equimolecular ratio.

The active ingredient is normally used as free acid, practically insoluble in water, in pharmaceutical compositions destined for oral use, while for alternative ways of administration, suitable Ketoprofen Salts with organic and inorganic bases are used. The Salts of Ketoprofen are usefully employed in the treatment of those pathological symptoms of rheumatoid and chronic type, which require the drug to be administered at high dosage, continuously and for long time. It is important and desirable that for the treatment of acute and very painful manifestations, there are pharmaceutical compositions suitable for immediate and manageable use, which rapidly release the active ingredient and are of high bio-availability. Typical examples of these compositions are those by parenteral administration and/or by oral administration, which allow a fine dispersion of the active ingredient.

The solubility and dissolution rate of drugs are decisive factors after oral administration for rate and extent of absorption.

These factors offer a key challenge for the development and formulation of effective drug in the pharmaceutical industry. The issue of poor drugs solubility—which is troublesome for synthesis and development as well—is known and is responsible for bioavailability problems.

Various strategies have been well documented to enhance solubility and dissolution of poorly soluble drugs such as Salt formation, solid dispersion, microemulsion, co-solvency, inclusion complex formation with cyclodextrin etc.

It is also possible to achieve desired properties of a particular active pharmaceutical ingredient (API) by forming a co-crystal of the API itself, or of a Salt of the API. Pharmaceutical co-crystallization has attracted great amount of academic, industrial and therapeutic interests by co-crystallization of two or more pure compounds with crystal engineering to create a new functional material.

Specifically, pharmaceutical co-crystals are defined as "co-crystals in which the target molecule or ion is an active pharmaceutical ingredient, API, and it bonds to the co-crystal former(s) through hydrogen bonds." (Almarsson M. and Zaworotko J., Chem. Commun., 2004: 1889).

Co-crystals can be also defined as a stoichiometric multi-component system formed between two or more compounds, which are solid under ambient conditions, connected by non-covalent and non-ionic interactions.

Pharmaceutical co-crystals are non-ionic supramolecular complexes and can be used to improve physiochemical property issues such as solubility, stability and bioavailability in pharmaceutical development without changing the chemical composition of the API.

Co-crystals containing API can be used to deliver API therapeutically. New drug formulations comprising co-crystals of API with pharmaceutically acceptable co-formers may, in some cases, have superior properties over existing drug formulations. However, co-crystal formation is not predictable and, in fact, not always possible. Moreover, there is no way to predict the properties of a particular co-crystal of a compound until it is formed. As such, finding the right conditions to obtain a particular co-crystal of a compound, with pharmaceutically acceptable properties, can take significant time, effort, and resources.

The documents GB1497044A and BE882889 describe the preparation of Salts of Ketoprofen with Lysine of formula

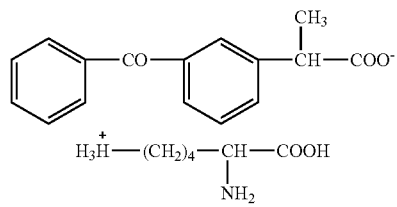

through a process in which non-saturated solutions of the components are used. However, the known Ketoprofen Lysine Salt shows a low crystallinity, possibly associated with undesired water uptake, and rather high particle size, as shown herein in FIG. 17 and at Table 13. These properties of Ketoprofen Lysine Salt may not be ideal in terms of stability and flowability of the powder or of dissolution profile and bioavailability.

SUMMARY OF THE INVENTION

The Applicant has unexpectedly found that Ketoprofen and Lysine, under certain process conditions, can form a co-crystal (herein named Form 1) which is highly crystalline and characterized by a lower particle size.

An object of the present invention thus refers to a co-crystal of Ketoprofen Lysine (Form 1) characterized by having an X ray diffraction pattern with characteristic peaks at 16.3; 17.5; 17.6; 17.7; 19.6; 19.7° 2theta, with a margin of error on the value indicated for each peak of ±0.20 degrees (2 theta).

Another object of the present invention is a pharmaceutical composition comprising the co-crystal of Ketoprofen Lysine (Form 1) of the present invention and one or more physiologically acceptable excipients.

Another object of the present invention is a pharmaceutical composition comprising the co-crystal of Ketoprofen Lysine (Form 1) of the present invention in combination with one or more pharmaceutically active agents.

Another object of the present invention refers to the co-crystal of Ketoprofen Lysine (Form 1) and to the pharmaceutical composition comprising said co-crystal for use as a medicament.

Another object of the present invention refers to the co-crystal of Ketoprofen Lysine (Form 1) and to the pharmaceutical composition comprising said co-crystal for the use in the treatment of pain and inflammatory diseases.

Another object of the present invention is a process for the production of the co-crystal of the present invention, wherein said process comprises the following steps:
  a) preparing a saturated solution of Ketoprofen;
  b) mixing the saturated solution with Lysine;
or
  $a_1$) preparing a saturated solution of Lysine in water;
  $b_1$) mixing the saturated solution with Ketoprofen.

8b. $^{13}$C (100 MHz) solid-state CPMAS spectra of Ketoprofen Lysine Salt in comparison with Ketoprofen, Lysine and Ketoprofen Lysine Co-crystal Form 1, acquired at a spinning speed of 12 kHz at room temperature.

Figure 9:
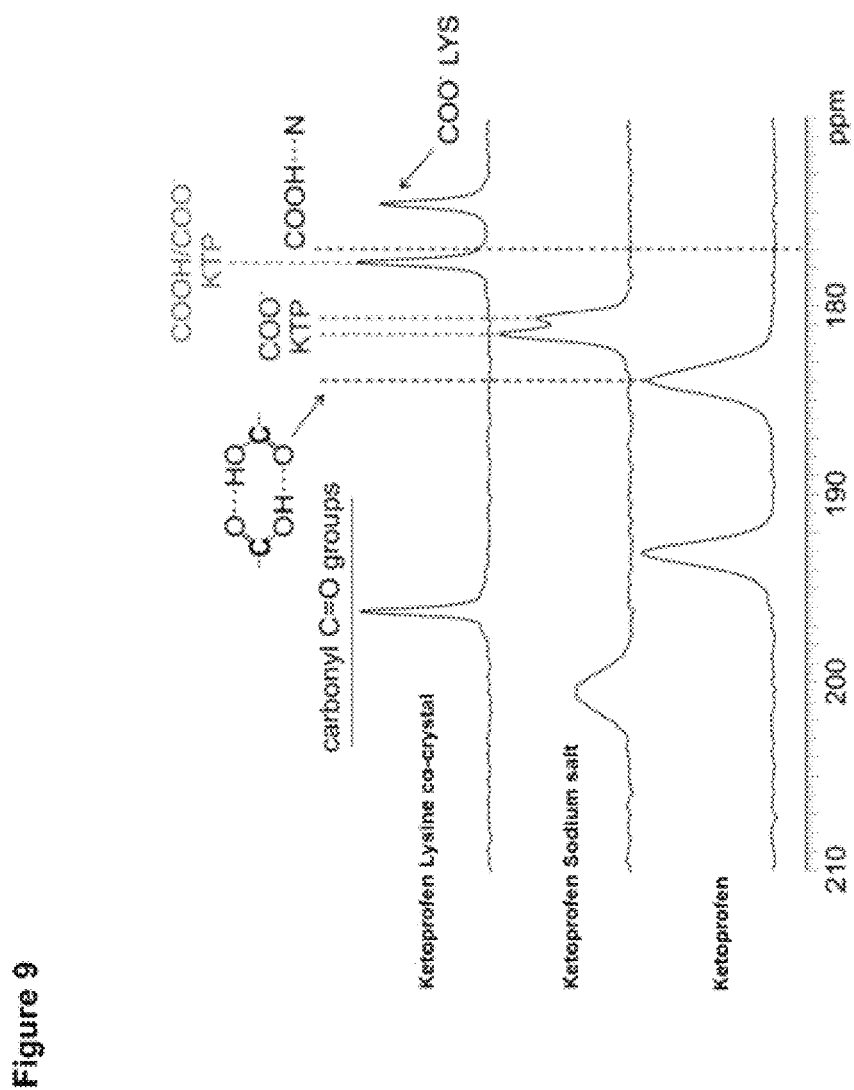

FIG. 9. $^{13}$C (100 MHz) CPMAS solid-state NMR spectra in the range 170-210 ppm of samples of racemic Ketoprofen, Ketoprofen Sodium Salt and Ketoprofen Lysine co-crystal Form 1 acquired at a spinning speed of 12 kHz at room temperature. The black dashed line at ca. 177 ppm refers to the chemical shift reported in literature for the protonated carboxylic group of ibuprofen, involved in a H-bond interaction with a nitrogen atom, in a (ibuprofen)2(4,4'-bipyridyl) co-crystal (Chen S.; Xi H.; Henry R. F.; Marsden I.; Zhang G. G. Z. Cryst Eng Comm 2010, 12, 1485-1493).

Figure 10:
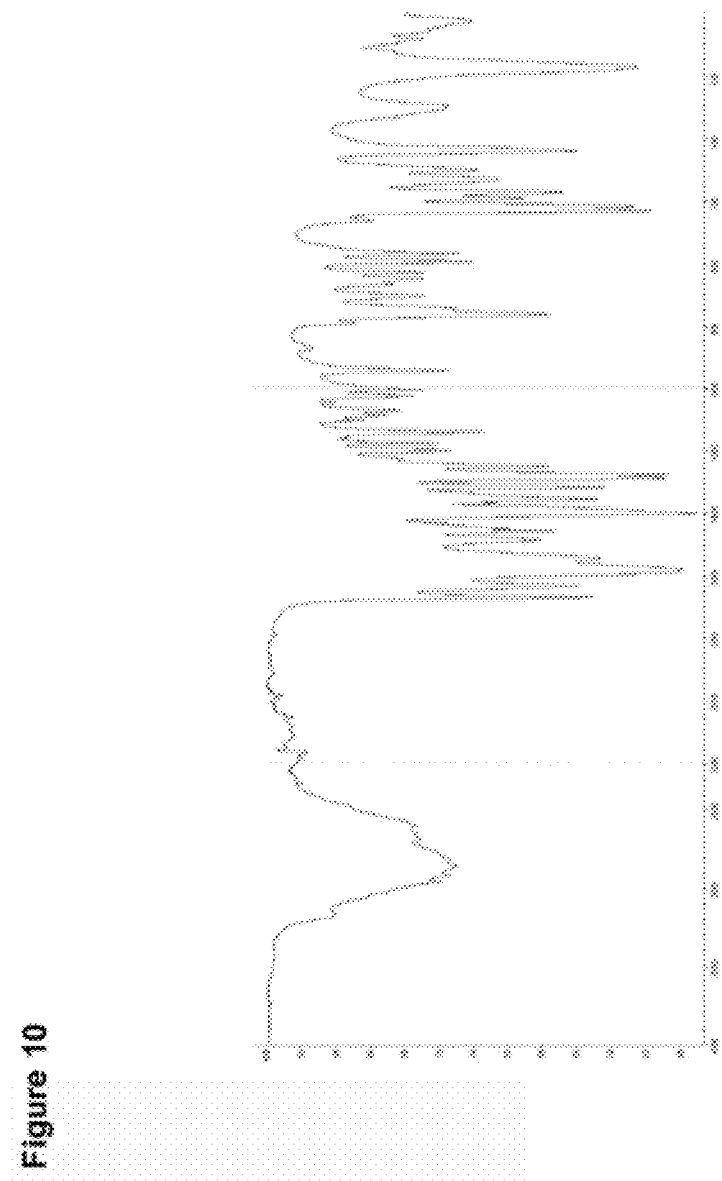

FIG. 10. FT-IR spectrum of Ketoprofen Lysine co-crystal Form 1.

Figure 11:
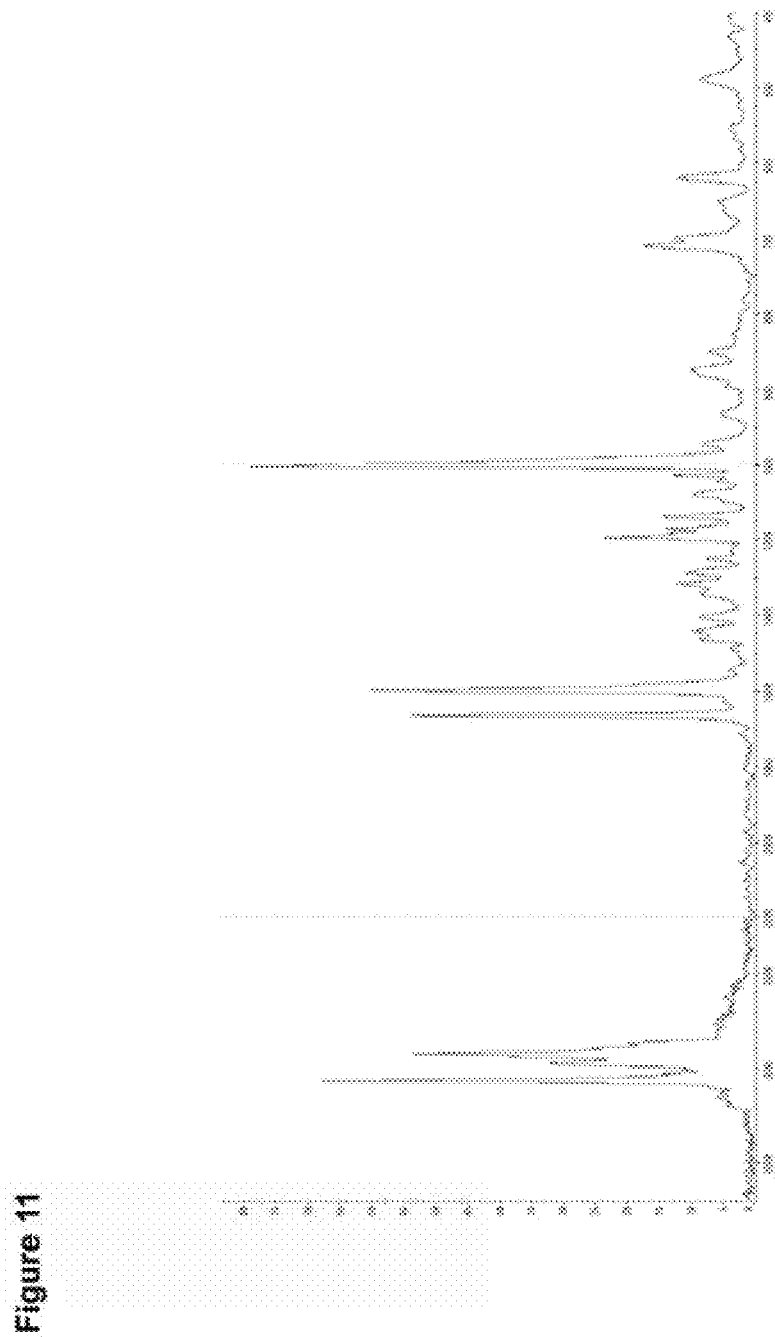

FIG. 11. FT-Raman spectrum of Ketoprofen Lysine co-crystal Form 1.

Figure 12:
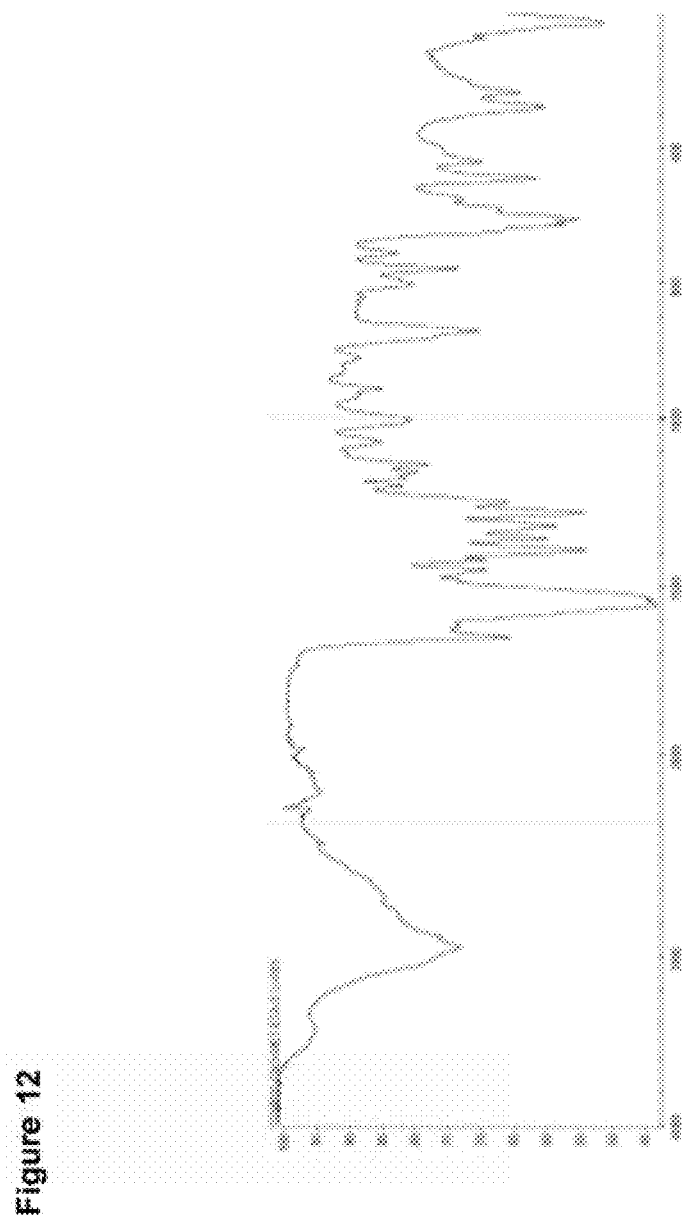

FIG. 12. FT-IR spectrum of comparative Ketoprofen Lysine Salt.

Figure 13:
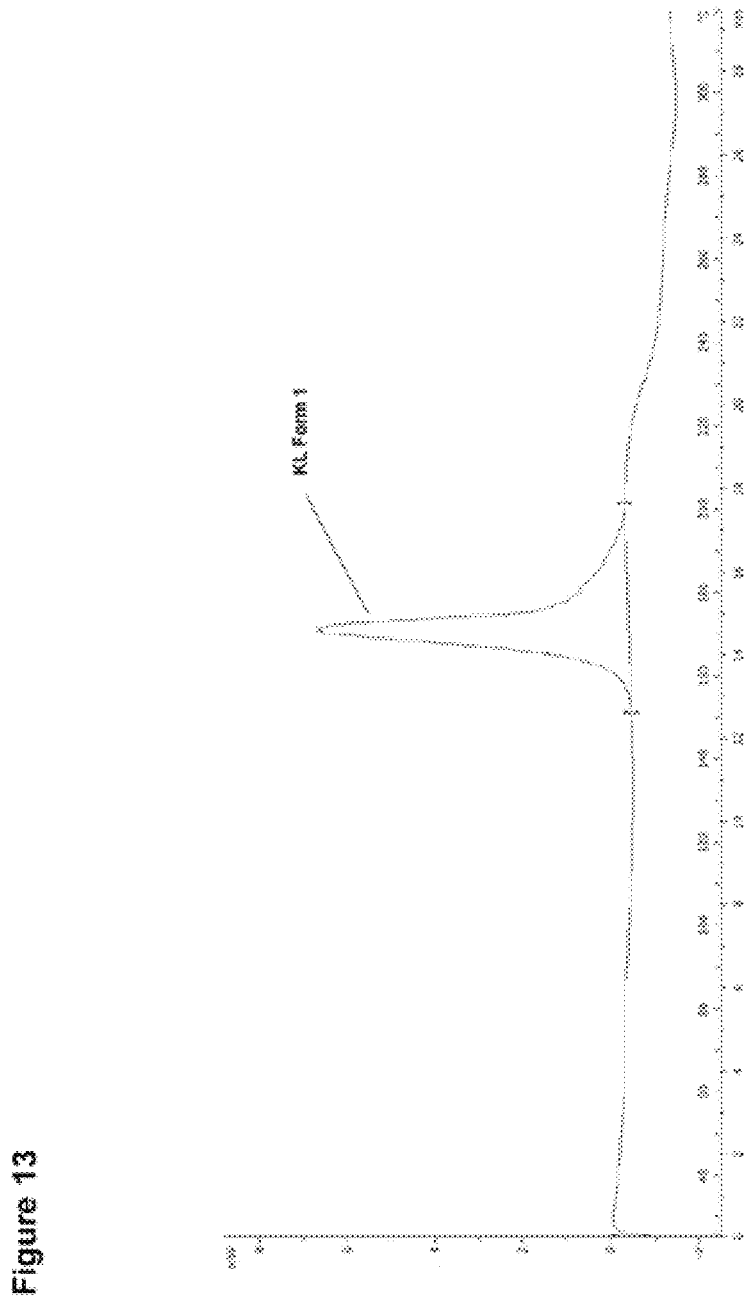

FIG. 13. DSC thermogram of Ketoprofen Lysine co-crystal Form 1.

Figure 14:
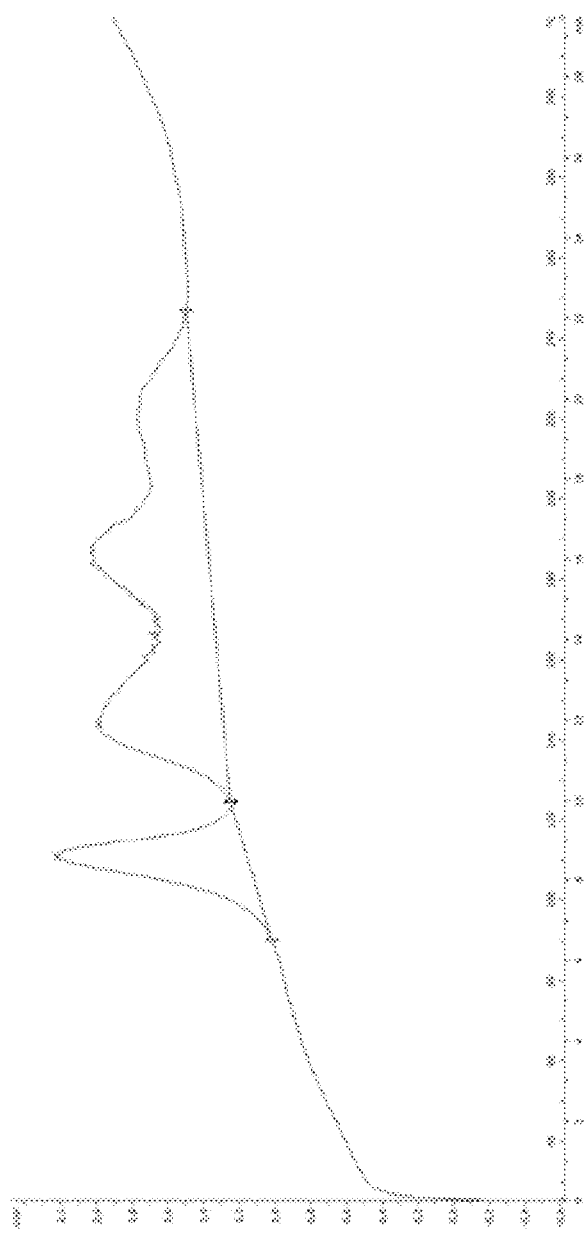

FIG. 14. DSC thermogram of Ketoprofen Lysine Salt.

Figure 15:
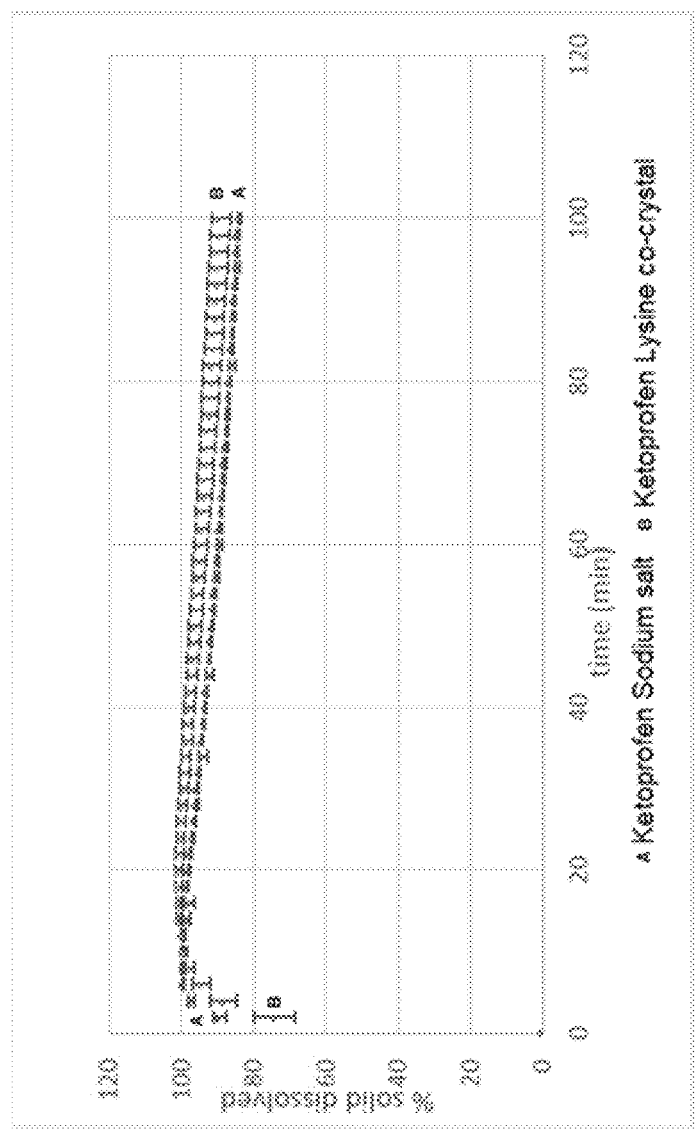

FIG. 15. Comparison between the dissolution of Ketoprofen Sodium Salt and Ketoprofen Lysine co-crystal Form 1.

Figure 16:
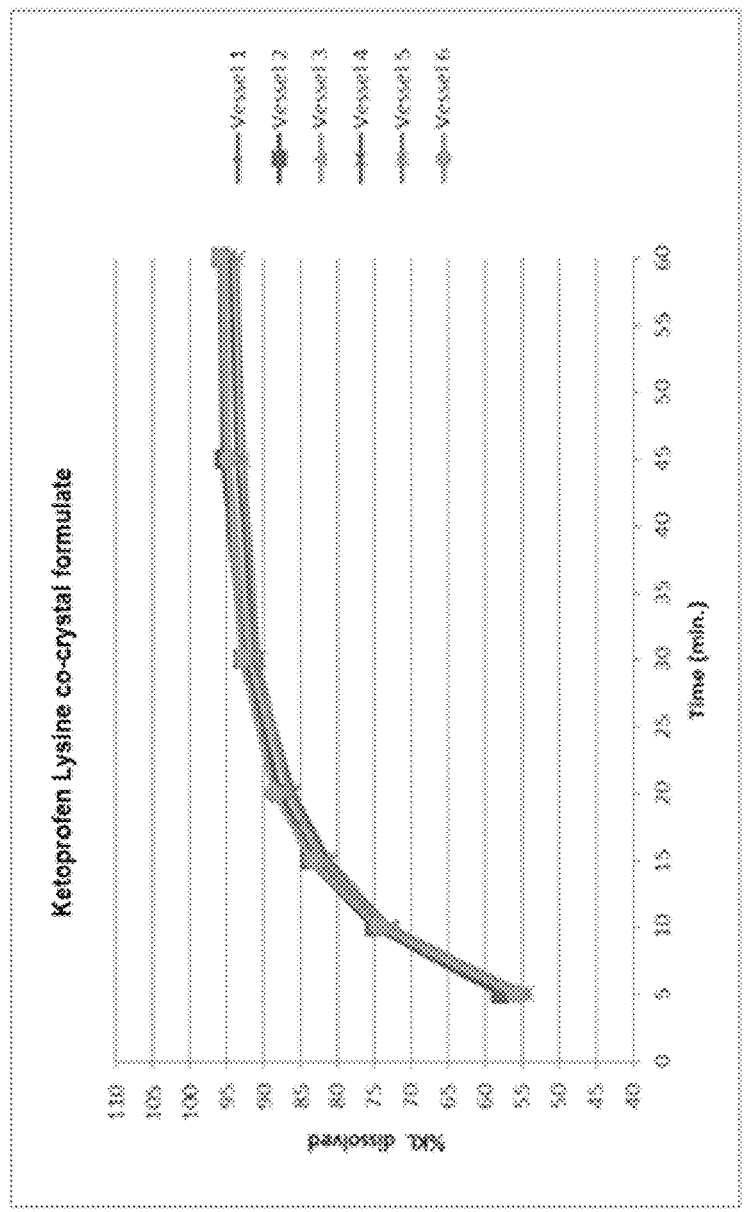

FIG. 16. Dissolution rate Ketoprofen Lysine co-crystal Form 1 (formulate).

Figure 17:
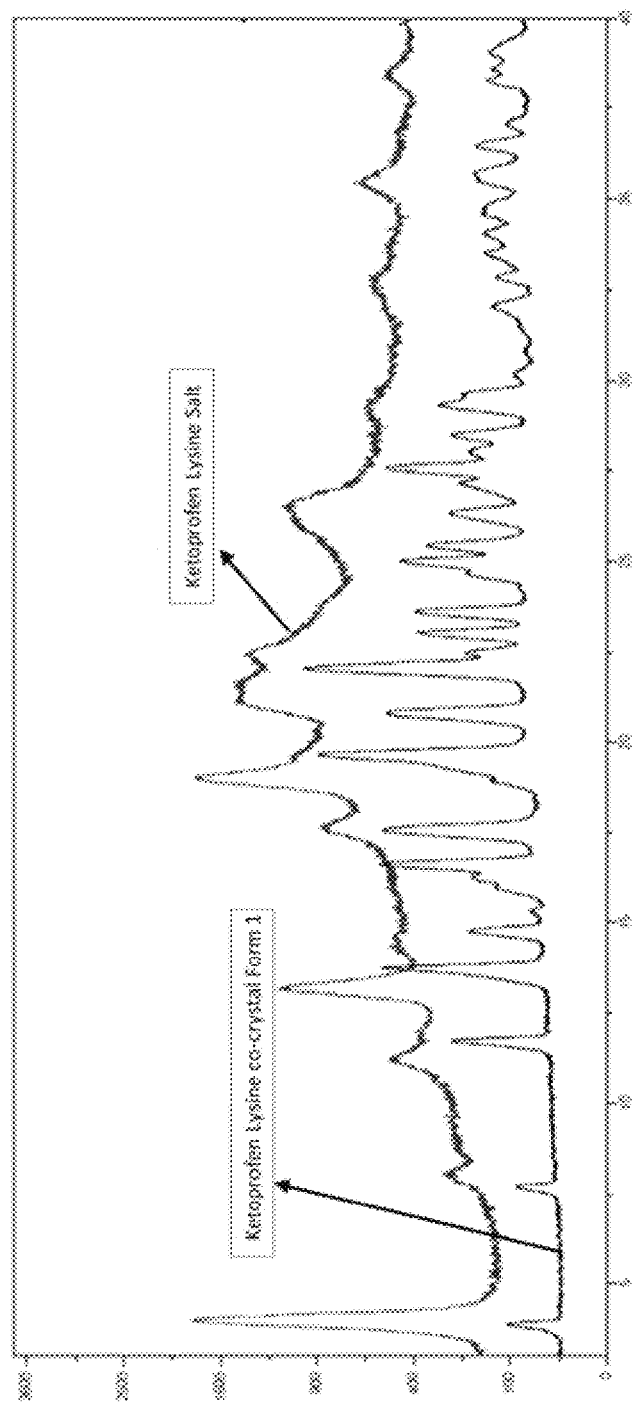

FIG. 17. XRPD pattern of Ketoprofen Lysine co-crystal Form 1 compared with Ketoprofen Lysine Salt.

DETAILED DESCRIPTION OF THE INVENTION

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

For the purpose of the present invention, the expression "room temperature" means a temperature range of 18-25° C.

For the purpose of the present invention the expression "co-crystal" means a stoichiometric multi-component system, in which the components are connected by non-covalent, non-ionic interactions and, individually, are solid under room conditions.

For the purpose of the present invention, the expression "pain" means pain caused by disturbances of different nature and origin, such as, for example: headache or cephalalgy: both primary and therefore not related to other factors or diseases, and secondary and therefore dependent on trauma, injury and distinct diseases; toothache: in case of abscesses or caries that create pain in the dental pulp, with numerous blood vessels and nerves; menstrual pains: abdominal and lower abdominal pain and headaches caused by hormonal changes typical of the period of menstruation; neuralgia, or intense nerve pain due to strains, trauma and infections; pain in the muscles, or myalgia: pains located at the level of muscles when using or touching them, due to sudden contractions or traumas; osteoarticular pains, such as joint inflammations (to the bones, cartilages, ligaments and tendons) following traumas, old age, strains and injuries.

The terms "approximately" and "about" herein refers to the range of the experimental error, which may occur in a measurement.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of".

The forms "consist essentially of", "consisting essentially of" are to be construed as semi-closed terms, meaning that no other ingredients which materially affects the basic and novel characteristics of the invention are included (optional excipients may thus be included).

The terms "consists of", "consisting of" are to be construed as closed terms.

The term "saturated solution" is to be construed as a chemical solution containing the maximum concentration of a solute dissolved in the solvent at a certain temperature. In the present context, if not otherwise stated, reference is made to room temperature.

A first object of the present invention refers to a co-crystal of Ketoprofen Lysine (Form 1) characterized by having an X ray diffraction pattern (XRPD) with characteristic peaks at 16.3; 17.5; 17.6; 17.7; 19.6; 19.7° 2theta, with a margin of error on the value indicated for each peak of ±0.20 degrees (2 theta).

Figure 4:
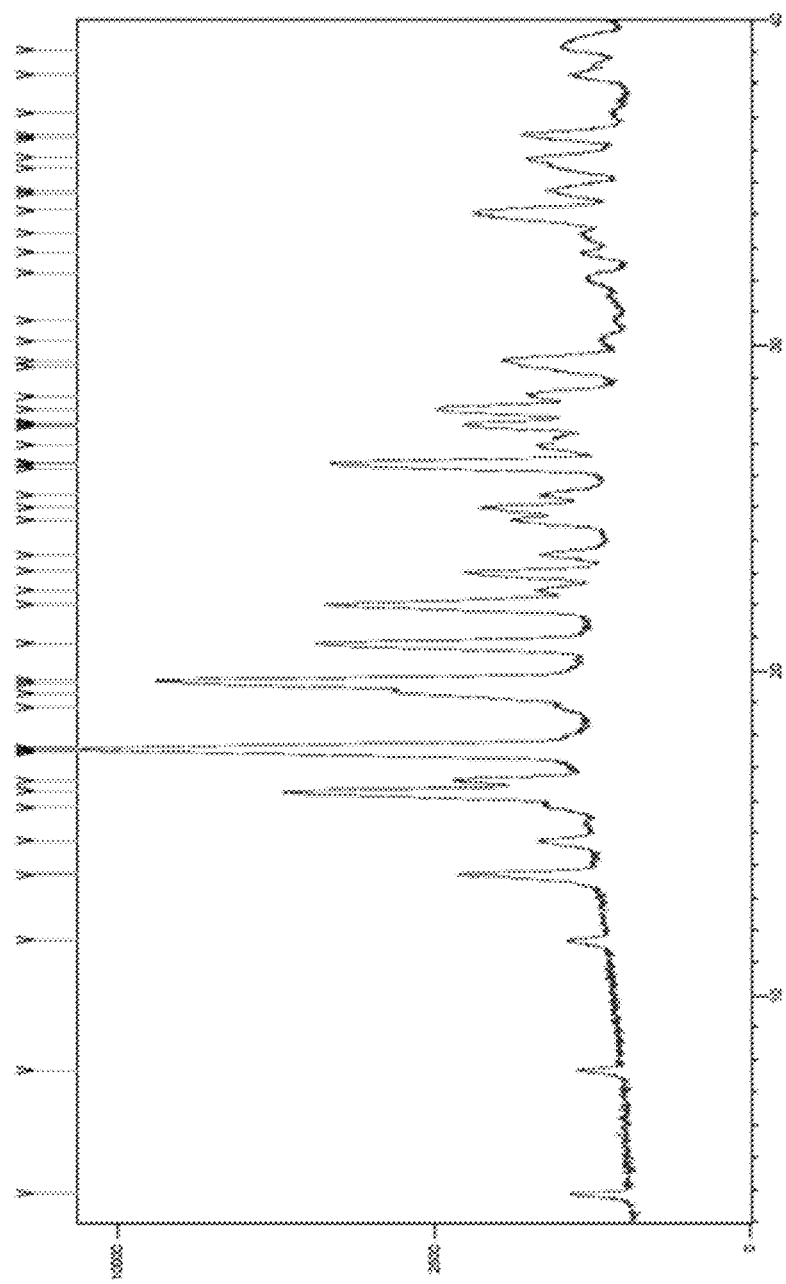
FIG. 4. XRPD pattern of Ketoprofen Lysine co-crystal Form 1 obtained with the process of saturated solutions of Lysine (ssLYS) in water.

The typical XRPD pattern of said co-crystal is represented in FIG. 4.

As reported in Table 4, the XRPD diffractogram shows relevant signals in the region from 17 to 25° 2theta.

In particular, Ketoprofen Lysine co-crystal Form 1 shows the most characterizing peaks at 16.2898; 17.4718, 17.5514; 17.6104; 17.6712; 19.5987; 19.7109° 2theta.

Figure 7:
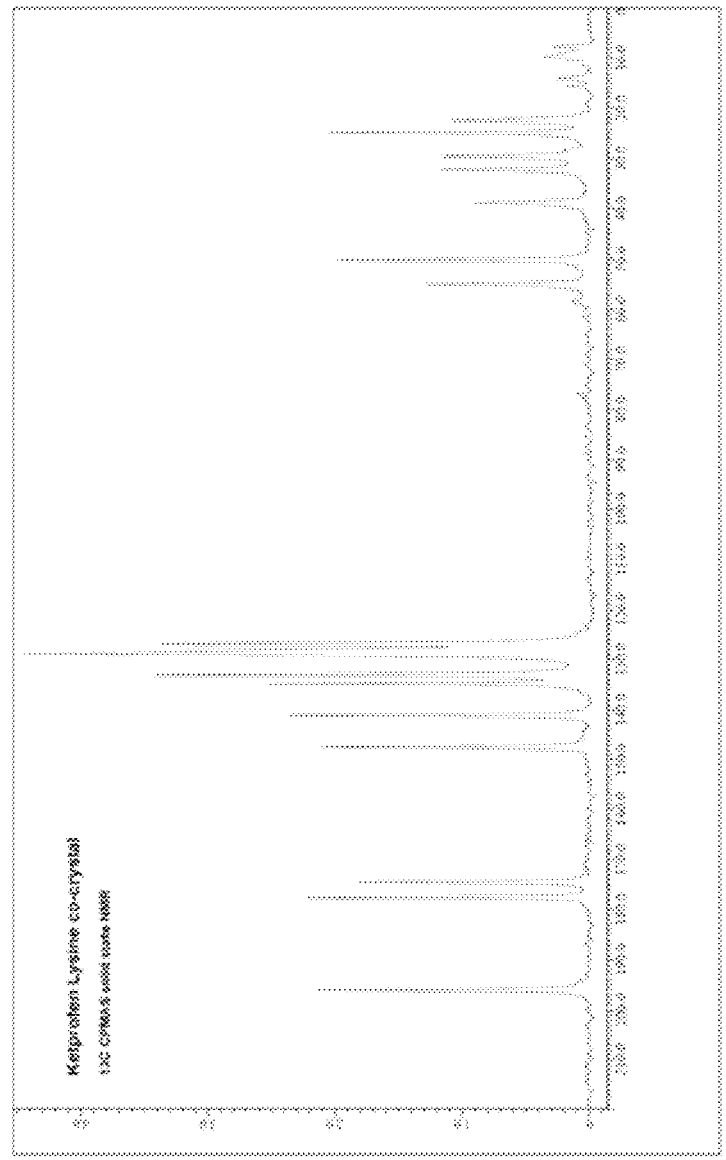
FIG. 7. NMR Spectra of Ketoprofen Lysine co-crystal Form 1. $^{13}$C (100 MHz) CPMAS solid-state NMR spectra acquired at a spinning speed of 12 kHz at room temperature.

In addition, the co-crystalline nature of Ketoprofen Lysine Form 1 of the present invention is shown in the $^{13}C$ ss-NMR (solid state NMR) spectra, so as depicted in FIG. 7 and Table 6A.

Preferably, the molecular ratio between Ketoprofen and Lysine of the co-crystal of the present invention is 1:1.

In order to determine said molecular ratio two software packages were used for the structure determination from powder diffraction data; Biovia Material Studio Reflex and EXPO2014, so as reported in the experimental section. These methodologies can be adopted for solving crystal structure by X-ray powder diffraction data. The collected powder is crystalline and the pattern was indexed with a monoclinic cell. Four Ketoprofen and four Lysine molecules were identified in the cell (1:1 stoichiometric ratio).

Preferably, the co-crystal of the present invention is co-crystal of (R)-2-(3-benzoylphenyl)-propionic acid D-Lysine.

Preferably, the co-crystal of the present invention is co-crystal of (R)-2-(3-benzoylphenyl)-propionic acid L-Lysine.

Preferably, the co-crystal of the present invention is co-crystal of (S)-2-(3-benzoylphenyl)-propionic acid D-Lysine.

Preferably, the co-crystal of the present invention is co-crystal of (S)-2-(3-benzoylphenyl)-propionic acid L-Lysine.

Figure 6:
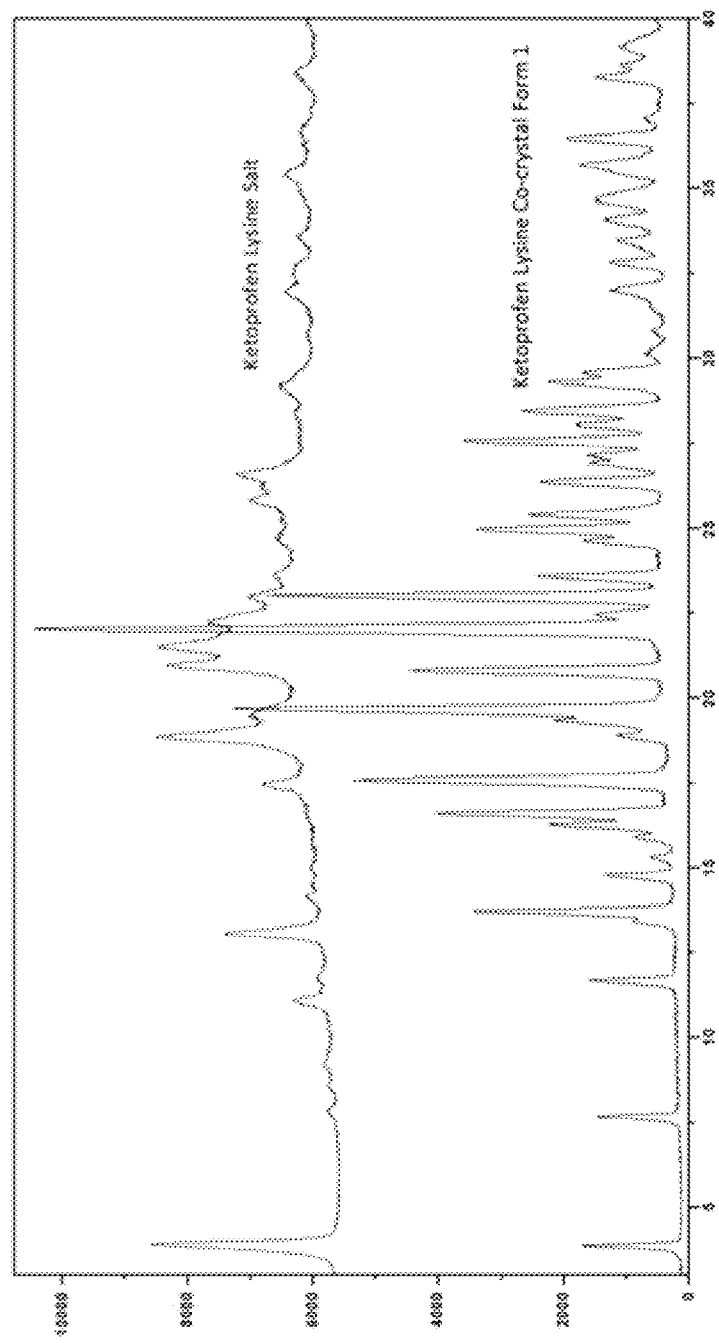
FIG. 6. Comparison between XRPD patterns of Ketoprofen Lysine Co-crystal Form 1 and Ketoprofen Lysine Salt.
Figure 8:
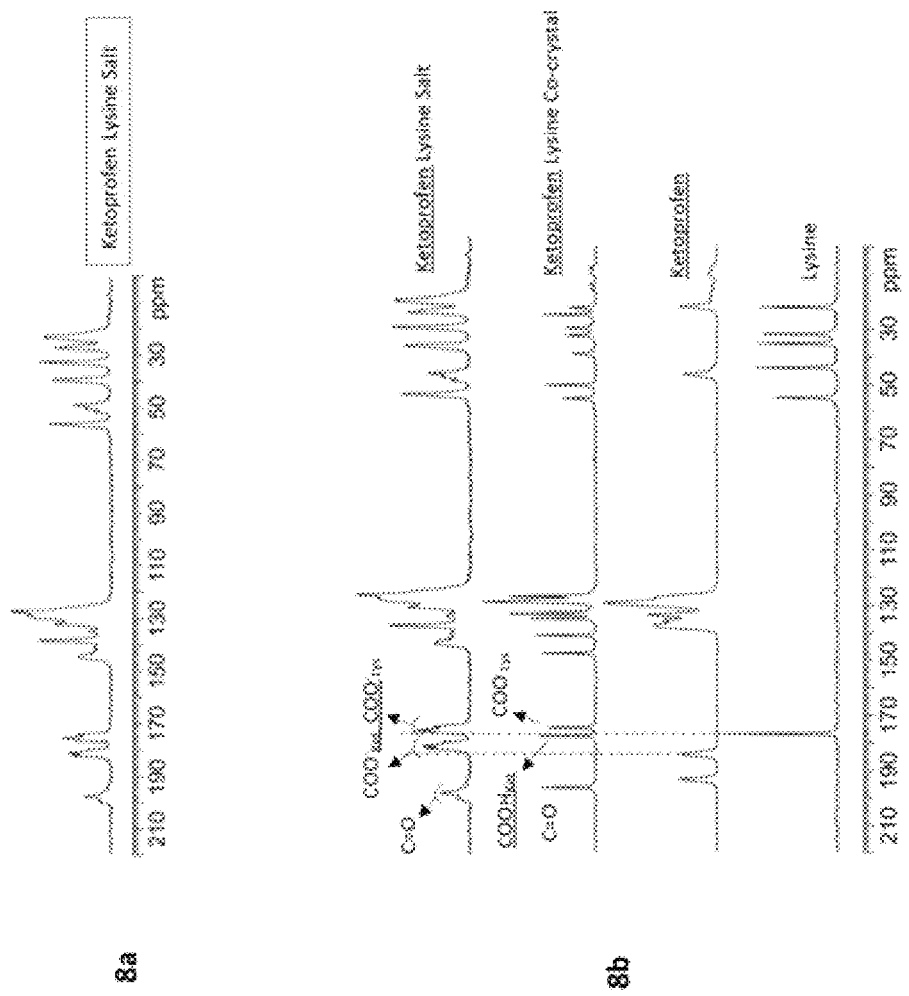
FIG. 8: 8a. $^{13}$C (100 MHz) solid-state CPMAS spectra of comparative Ketoprofen Lysine Salt, acquired at a spinning speed of 12 kHz at room temperature.

The co-crystal of Ketoprofen Lysine (Form 1) of the present invention differs from Ketoprofen Lysine Salt as shown in the XRPD comparison of FIG. 6, in the $^{13}C$ CPMAS solid-state NMR comparison of FIG. 8b and in FT-IR comparison of FIGS. 10 and 12.

Advantageously, the co-crystal of Ketoprofen Lysine of the present invention shows a high dissolution rate, so as reported in FIG. 15.

Thus, the high dissolution rate of the co-crystal of Ketoprofen Lysine Form 1 of the present invention allows its use in the treatment of those pathological and chronic symptoms, which require the drug to be administered at high dosage, continuously and for long period of time.

Furthermore, the co-crystal of Ketoprofen Lysine Form 1 of the present invention shows lower particle size, as reported in Table 13, and greater crystallinity than previous Ketoprofen Lysine Salt, as shown in FIG. 17.

Preferably, the co-crystal Form 1 according to the present invention has a particle size distribution with a D90 lower than 300 μm, preferably lower than 250 μm, more preferably lower than 200 μm.

Preferably, the co-crystal Form 1 according to the present invention has a particle size distribution with a D90 from 100 μm to 300 μm, preferably from 150 to 250 μm, more preferably 170 μm to 200 μm.

These properties are advantageous in the setting of the fluid-dynamic process parameters during the production of the coated granulate of Ketoprofen Lysine. The evaluation of the dynamic flow and the shear properties as well as stability of the powder through tests such as basic stability energy, stability index, specific energy and conditioned bulk density shows greater friction phenomena in the powder bed for Ketoprofen Lysine Salt compared to Co-crystal. The phenomenon could be derived from the greater amorphous degree, the irregular shape and the higher hygroscopicity of the Ketoprofen Lysine Salt compared to the present Co-crystal. Another object of the present invention refers to pharmaceutical compositions comprising the co-crystal of Ketoprofen Lysine Form 1 of the present invention.

The pharmaceutical composition of the present invention is suitable for immediate and manageable use, and rapidly releases the API.

Preferably, the pharmaceutical composition of the present invention further comprises physiologically acceptable excipients.

More preferably, said excipients are selected from the group consisting of: povidone, colloidal silica, hydroxypropylmethylcellulose, Eudragit® EPO, sodium dodecyl sulfate, stearic acid, magnesium stearate, aspartame, mannitol, xylitol, talc, flavors.

Preferably, the pharmaceutical composition of the present invention is in a solid form, more preferably in solid granulate form.

As reported in FIG. 16, the solid granulate form of the co-crystal of Ketoprofen Lysine Form 1 shows high dissolution rate.

Another object of the present invention is the co-crystal of Ketoprofen Lysine Form 1 and the pharmaceutical composition comprising said co-crystal for medical use, preferably for use in the treatment of pain and inflammation diseases.

Preferably, the co-crystal of Ketoprofen Lysine Form 1 and the pharmaceutical composition comprising said co-crystal are used in the treatment of pain, in which the pain is selected from the group consisting of: acute pain, headache, toothache, menstrual pain, muscle pain, osteoarticular pain.

Preferably, the co-crystal of Ketoprofen Lysine Form 1 and the pharmaceutical composition comprising said co-crystal are used in the treatment of inflammation diseases, in which the inflammation diseases are selected from the group consisting of rheumatic diseases.

Advantageously, the co-crystal of the present invention can be obtained by starting from a saturated solution.

Another object of the present invention is a pharmaceutical composition comprising the co-crystal of Ketoprofen Lysine (Form 1) of the present invention in combination with one or more pharmaceutically active agents.

Another object of the present invention is a process for the production of the co-crystal of the present invention, wherein said process comprises the following steps:

a) preparing a saturated solution of Ketoprofen;
b) mixing the saturated solution with Lysine;

or a$_1$) preparing a saturated solution of Lysine in water;
b$_1$) mixing the saturated solution with Ketoprofen.

Advantageously, with the process of the present invention a significantly high yield is obtained, so as reported in Table 3A. Preferably, the equivalent ratio between saturated Ketoprofen and Lysine or between saturated Lysine and Ketoprofen is 3:1 or higher.

Preferably, in the process comprising the steps a) and b) (process 2.c.i in the experimental part), the equivalent ratio between Ketoprofen in the saturated solution and Lysine is from 10:1 to 1:1, more preferably from 3:1 to 1:1.

Preferably, in the process comprising the steps a) and b), the ratio between the amount of Lysine by weight (mg) and the volume (ml) of the saturated solution of Ketoprofen is comprised between 1 mg/ml and 90 mg/ml, preferably from 4 mg/ml to 70 mg/ml, more preferably from 5 mg/ml to 60 mg/ml.

Preferably, the solvent used for the saturated solution of Ketoprofen is selected from the group consisting of: alcohols, ethers, esters, amides, ketones, aromatic solvents, halogenated solvents and aprotic dipolar solvents.

More preferably, said alcohols are selected from the group consisting of: ethanol, methanol, 1-butanol, 1-propanol, 2-butanol, 2-propanol, 1-pentanol and benzyl alcohol.

More preferably, said ethers are selected from the group consisting of: 1,4-dioxane and tetrahydrofuran.

More preferably, said esters are selected from the group consisting of: ethyl acetate, methyl acetate, propyl acetate.

More preferably, said amides are selected from the group consisting of: N,N, dimethylacetamide and 1-methyl-2-pirrolidone.

More preferably, said ketones are selected from the group consisting of: acetone, cyclopentanone, 4-Methyl-2-Pentanone.

More preferably, said aromatic solvents are selected from the group consisting of: toluene, benzonitrile, p-xylene.

More preferably, said halogenated solvents are selected from the group consisting of: dichloromethane, 1,2-dichloroethane and chloroform.

More preferably, said aprotic dipolar solvents are selected from the group consisting of:
dimethylsulphoxide, acetonitrile.

Admixtures of two or more of the above solvents can be used as well.

Preferably, said mixing step b) or b$_1$) is carried out at a temperature from 5° C. to 30° C., more preferably at room temperature.

Preferably, said mixing step b) or b1) is carried out, preferably by stirring, at a temperature from 15° C. to 30° C., for 10 to 72 hours, more preferably by stirring at room temperature for 24 hours.

The co-crystal of the present invention can be also obtained by evaporation (process 2.a of the present experimental part). Said process comprises the step of:
a') mixing Ketoprofen and Lysine in a halogenated solvent up to provide a solution, wherein said Ketoprofen is in stoichiometric excess in comparison to Lysine;
b') evaporating the solution obtained from step a') to provide a solid, and
c') optionally slurrying the solid in a solvent.

Preferably, the equivalent ratio between Ketoprofen and Lysine of step a') is 8:1 or higher.

Preferably, said halogenated solvent is selected from the group consisting of: dichloromethane, chloroform, 1,2-dichloroethane. More preferably, said solvent is dichloromethane.

Preferably, said mixing is carried out by stirring for 1 hour at room temperature.

Preferably, said evaporating of step b') is carried out at room temperature.

Preferably, the solution of step a') is filtered before step b').

Preferably, the slurrying of step c') is carried out in a solvent selected from isopropyl ether, 2-Methyl-1-Propanol, Methyl Ethyl Ketone.

Advantageously, with said alternative process a high yield is obtained by using dichloromethane as the halogenated solvent so as reported in Table 1.

The co-crystal of the present invention can be also obtained by a process involving a precipitation technique (process 2.b of the experimental part). Said process comprises the following steps:
a") mixing an aqueous solution of Lysine with a Ketoprofen solution,
b") adding the solvent of the Ketoprofen solution until a solid is formed.

Preferably, said process comprises the following steps:
a") mixing an aqueous solution of Lysine with a non-aqueous Ketoprofen solution in a non-aqueous solvent, to provide an admixture,
b") adding the non-aqueous solvent of the Ketoprofen solution to the admixture until a solid is formed.

With the term "non-aqueous solution" a solution comprising less than 10%, preferably, less than 5%, more preferably less than 1%, even more preferably less than 0.5% or 0.1% ww of water is meant.

Preferably, the Ketoprofen and Lysine of step a") are in 1:1 equivalents ratio. Preferably, the non-aqueous solvent of said Ketoprofen non-aqueous solution is selected from the group consisting of alcohols, ethers, amides and ketones, as above listed.

Preferably, said steps a") and b") are carried out at room temperature. The co-crystal of the present invention can be also obtained by a process involving another precipitation technique (process 2.c.ii of the experimental part). Said process comprises the following steps
a''') preparing a non-saturated solution of Ketoprofen in a solvent selected from the group consisting of Acetone, Chloroform, Cyclopentanone, 1,4-Dioxane, DMSO, Ethanol, Methanol, 1-Methyl-2-Pyrrolidone and Tetrahydrofuran;
b''') mixing the non-saturated solution of Ketoprofen with Lysine, wherein the equivalent ratio between Ketoprofen and Lysine is 3:1.

As can be seen in the experimental part (Table 3B), a variation in the equivalent ratio between Ketoprofen and Lysine does not provide the desired product. Preferably, the non-saturated solution of step a''') has a concentration of Ketoprofen from 400 mg/ml to 250 mg/ml, more preferably from 350 mg/ml to 250 mg/ml.

Experimental Part

In the following, some non-limitative examples are provided related to the computational calculation and production process of the co-crystal of Ketoprofen Lysine Form 1, its yields, XRPD analysis, NMR analyses, FT-IR analysis, RAMAN analysis, dissolution rate and particle size distribution.

Furthermore, comparative examples with Ketoprofen Sodium Salt and Ketoprofen Lysine Salt, their analytical characterization and their comparison of properties are provided.

1. Computational Study

Two software packages were used for the structure determination from powder diffraction data:
Biovia Material Studio Reflex; and
EXPO2014.

These methodologies can be adopted for solving crystal structure by X-ray powder diffraction data. Four Ketoprofen and four Lysine molecules were identified in the cell (calculated volume 2111 Å$^3$).

The space group was assigned checking the systematic absences in the first part of the pattern. The reflections 0 0 l (l=2n+1), 0 k 0 (k=2n+1) and h 0 l (l=2n+1) have zero intensity which suggest the space group P2$_{1/c}$ with only one couple Ketoprofen-Lysine forming the asymmetric unit.

Starting from a high-quality powder containing of Ketoprofen Lysine, a correct solution has been achieved with an enough correlation between experimental powder pattern and the simulated one. Material Studio Reflex (1) available from BIOVIA and EXPO2014 (2) software, has been applied.

Biovia Material Studio Reflex allows to indexing the experimental powder by using accurate methods: TREOR90 (3), DICVOL91 (4), and ITO (5), determining the cell parameters and crystal system. After that, the Pawley (6) refinement helps to refines the cell parameters, peak shape, and background values. Some specific settings such as weighted R-factor and R$_{wp}$ (weighted profile R-factor) are optimized in order to get agreement between the experimental and simulated powder diffraction pattern. The next step involves the powder solving. Material Studio Reflex go through an indirect method that employs a Monte Carlo simulated annealing or parallel tempering algorithms. This obtained simulated pattern is then compared to the experimental powder pattern using R$_{wp}$ as a measure of similarity. Structures with low R$_{wp}$ values are automatically saved to trajectory files. Multiple cycles to determine the structure are performed to confirm the final solution. A final refinement of the proposed solution is performed with the rigid-body Rietveld (7; 8) refinement. EXPO2014 allow to obtain the crystal structure solution via "Direct Methods" and/or by a direct-space approach, and the structure refinement by the Rietveld technique. The first step includes the indexing process carried out with program N-TREOR09 (9), followed by space-group determination analysis. To solve the correct solution, we used a specific direct-space technique, such as simulated annealing (SA), ensuring to directly accommodate the structure model by using the fitting between the experimental and calculated profile. The SA approach tries to solve crystal structures by moving a molecular model in the monoclinic cell, adjusting its orientation until the minimum of a suitable cost function, is reached. The last step in the ab initio crystal structure solution is the completion and refinement of the structure model. In the case of powder data the Rietveld (7) method is the most popular technique.

2. Production Processes 2.a Evaporation

The experiments were performed preparing a clear solution of racemic Lysine and racemic Ketoprofen.

In order to prepare the solution, 29 mg of Lysine and 50 mg of Ketoprofen were weighed in a 8 mL vial and 5 mL of Dichloromethane was added.

Since Lysine was not soluble in these conditions, Ketoprofen was added portion-wise to promote Lysine dissolution.

Eight equivalents of Ketoprofen were added and the solution of Lysine (1 equivalent) in dichloromethane, stirred for 1 hour at room temperature, filtered and left to evaporate at 25° C.

A sticky solid was recovered after the experiment, so it was further slurried in 2 mL of Isopropyl Ether (IPE) for 48 hours.

Figure 1:
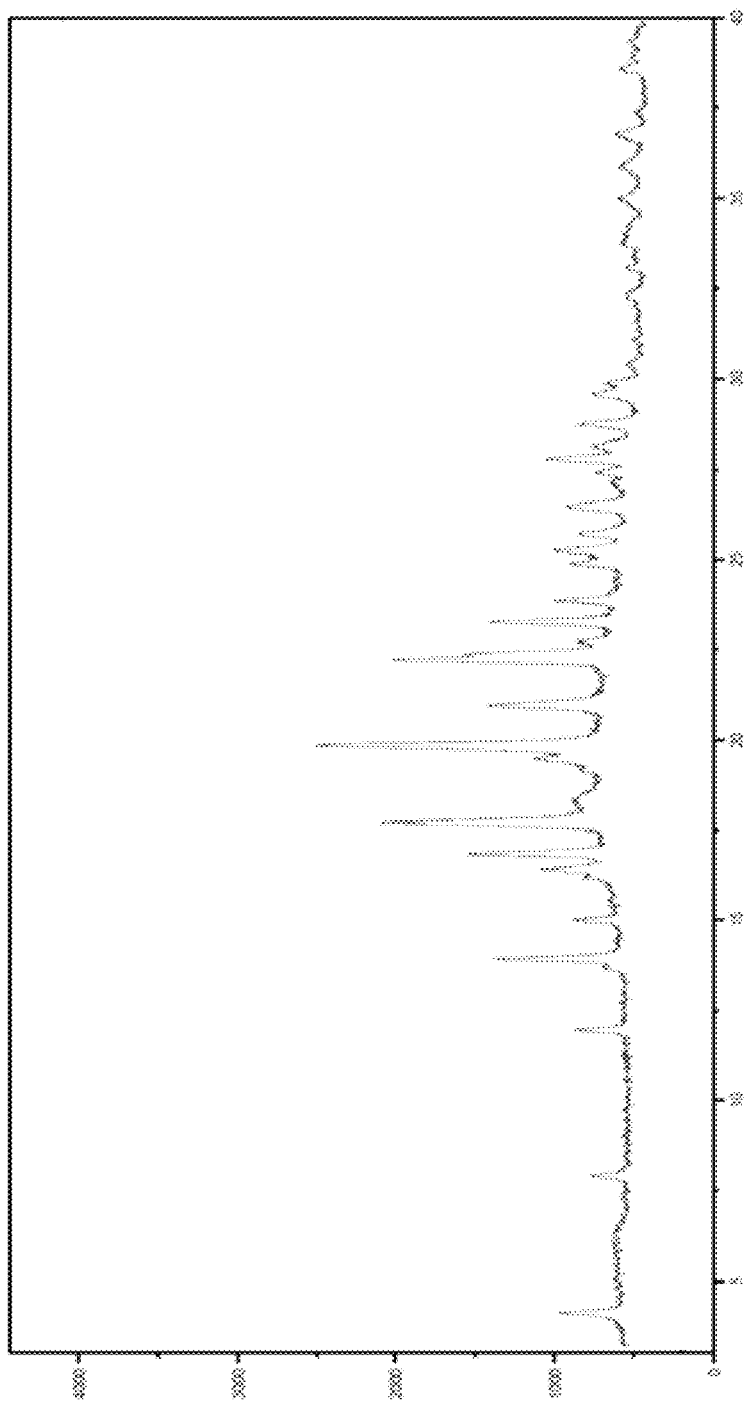
FIG. 1. XRPD of the Ketoprofen-Lysine co-crystal Form 1 collected after evaporation experiment in Dichloromethane.

After this time, a white solid was isolated with a yield of 90% and analyzed by XRPD. The presence of Ketoprofen-Lysine co-crystal Form 1 was observed, as reported in FIG. 1.

The same evaporation experiment, has been carried out in the same conditions, but using chloroform and 1,2-dichloroethane instead of dichloromethane. As reported in the Table 1, the yield is better by using dichloromethane.

TABLE 1

Results of evaporation tests

| Solvent | KET eq. | T (° C.) | Aspect after Evaporation | XRPD | Yield (%) |
|---|---|---|---|---|---|
| Dichloromethane | 8 | 25 | Sticky solid, slurry in IPE | KET-LYS | 90 |
| Chloroform | 8 | 25 | Sticky solid, slurry in IPE | KET-LYS | 68 |
| 1,2-Dichloroethane | 8 | 25 | Sticky solid, slurry in IPE | KET-LYS | 60 |

2.b Precipitation

Precipitation experiments were performed by preparing a solution of Lysine in water and solutions of Ketoprofen in selected solvents (see Table 2), then adding dropwise these to aqueous solution of racemic Lysine. 29 mg of Lysine (0.198 mmol) were dissolved in 0.1 mL of water, while 50 mg (0.198 mmol, 1 eq.) of Ketoprofen was dissolved in 0.5 mL of the selected solvent (see Table 2), also used as anti-solvent for the precipitation.

After the addition of Ketoprofen, the solution was stirred for 15 minutes, and if no precipitation was observed, more solvent was added dropwise until the formation of a solid.

Figure 2:
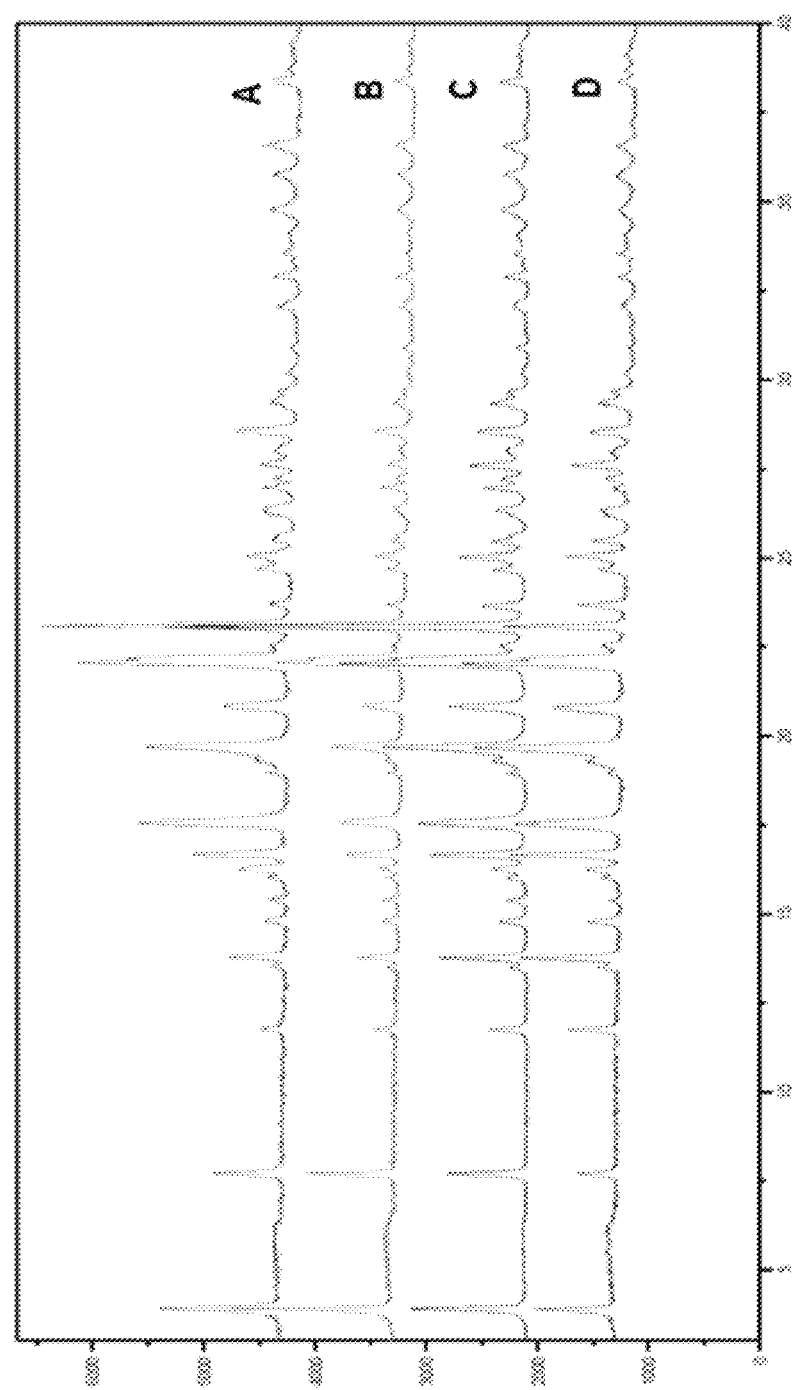
FIG. 2. XRPD of the Ketoprofen-Lysine co-crystal Form 1 collected after precipitation experiments in 1,4-Dioxane (DIX, A), Acetone (ACT, B), Acetonitrile (ACN, C) and N-Methyl Pyrrolidone (NMP, D).

After this time, a white solid was isolated and analyzed by XRPD. The presence of Ketoprofen-Lysine co-crystal Form 1 was observed, as reported in the following Table 2 and FIG. 2.

TABLE 2

Results of precipitation experiments Stoichiometric Ratio Ketoprofen: Lysine 1:1

| Solvent | mL of solvent added | XRPD | Yield (%) |
|---|---|---|---|
| 1-Butanol | 1 | KET-LYS | 72 |
| 1-Pentanol | 2 | KET-LYS | 60 |
| 1-Propanol | 1 | KET-LYS | 68 |
| (±) 2-Butanol | 1 | KET-LYS | 66 |
| 2-Propanol | 1 | KET-LYS | 60 |
| Acetonitrile | 1 | KET-LYS | 65 |
| Acetone | 1 | KET-LYS | 63 |
| 1,4-Dioxane | 1 | KET-LYS | 52 |
| N,N-Dimethylacetamide | 1 | KET-LYS | 58 |
| N,N-Dimethylformamide | 1 | KET-LYS | 55 |
| 1,2-Dimetoxy Ethane | 1 | KET-LYS | 50 |
| Ethanol | 1 | KET-LYS | 78 |
| Methanol | 3 | KET-LYS | 68 |
| 2-Methyl Propanol | 1 | KET-LYS | 70 |

TABLE 2-continued

Results of precipitation experiments Stoichiometric Ratio Ketoprofen: Lysine 1:1

| Solvent | mL of solvent added | XRPD | Yield (%) |
|---|---|---|---|
| N-Methyl-2-Pyrrolidone | 1 | KET-LYS | 56 |
| Tetrahydrofuran | 3 | KET-LYS | 54 |

2.c.i Crystallization from Ketoprofen Saturated Solution

The experiments wore performed by adding a saturated solution of Ketoprofen to 29 mg of racemic Lysine. Saturated solutions were prepared by dissolving 50 mg of Ketoprofen in the selected solvent (see Table 3) in an 8 mL glass vial equipped with a magnetic stirring bar at room temperature.

The solution was stirred until complete dissolution of the solid. More Ketoprofen was then manually added to the solution until no further Ketoprofen dissolved.

The solution was left to equilibrate for approx. 4 hours and the final solution was withdrawn from the vial using a plastic syringe and filtered using a 0.45 μm syringe filter to remove any excess solid.

The filtered solution was then added to racemic Lysine (29 mg, 0.198 mmol) and the resulting mixture was stirred at room temperature for 24 hours.

After this time, a small amount of the formed solid was recovered and analyzed by XRPD. When no solid was recovered, the solution was left to evaporate unfit the formation of a solid was observed.

The results observed after these experiments are reported in the Table 3A.

TABLE 3A

Results of crystallization experiments from Ketoprofen saturated solution

| Solvent | Volume of ssKET (mL) | XRPD | Yield |
|---|---|---|---|
| 1-Butanol | 0.5 | KET-LYS | 70 |
| 1-Pentanol | 0.5 | KET-LYS | 62 |
| 1-Propanol | 0.5 | KET-LYS | 67 |
| (±) 2-Butanol | 0.5 | KET-LYS | 62 |
| 2-Propanol | 0.5 | KET-LYS | 67 |
| Benzyl Alcohol | 0.5 | KET-LYS | 80 |
| Benzonitrile | 0.5 | KET-LYS | 68 |
| Dichloromethane | 0.5 | KET-LYS | 88 |
| N,N-Dimethylacetamide | 0.5 | KET-LYS | 53 |
| Ethyl Acetate | 0.5 | KET-LYS | 75 |
| Methyl Acetate | 0.5 | KET-LYS | 72 |
| 4-Methyl-2-Pentanone | 0.5 | KET-LYS | 69 |
| Propyl Acetate | 0.5 | KET-LYS | 70 |
| p-Xylene | 5.0 | KET-LYS | 31 |
| Toluene | 1.5 | KET-LYS | 32 |

2.c.ii Crystallization from Ketoprofen Solution with Equivalent Ratio KET:LYS 3:1

In case of Acetone, Chloroform, Cyclopentanone, 1,4-Dioxane, Dimethyl Sulphoxide, Ethanol, Methanol, 1-Methyl-2-Pyrrolidone and Tetrahydrofuran, 150 mg of Ketoprofen (3 eq.) were completely dissolved in 0.5 mL of the proper solvent, then the solution was added to 29 mg (0.198 mmol) of Lysine. The mixture was so stirred for 24 hours at room temperature, and the obtained solid was isolated and analyzed by XRPD.

When no solid material precipitated after 24 hours, the clear solution was left to evaporate until the formation of a solid was observed.

The results of these experiments are collected in Table 3B:

TABLE 3B

| Solvent | Stoichiometric ratio Ketoprofen: Lysine | Volume of Ketoprofen solution (mL) | XRPD | Yield |
|---|---|---|---|---|
| Acetone | 3:1 | 0.5 | KET-LYS | 73 |
| Chloroform | 3:1 | 0.5 | KET-LYS | 75 |
| Cyclopentanone | 3:1 | 0.5 | KET-LYS | 69 |
| 1,4-Dioxane | 3:1 | 0.5 | KET-LYS | 51 |
| DMSO | 3:1 | 0.5 | KET-LYS | 52 |
| Ethanol | 3:1 | 0.5 | KET-LYS | 85 |
| Methanol | 3:1 | 0.5 | KET-LYS | 75 |
| 1-Methyl-2-Pyrrolidone | 3:1 | 0.5 | KET-LYS | 68 |
| Tetrahydrofuran | 3:1 | 0.5 | KET-LYS | 50 |
| Acetone | 2:1 | | No co-xx | — |

Crystallization experiments in Benzyl Alcohol and Dichloromethane furnished a clear solution, therefore evaporation experiments were performed in order to collect a solid.

The solutions in Benzyl Alcohol was left to evaporate at high temperature (60° C.), while Dichloromethane solution was evaporated at room temperature.

Figure 3:
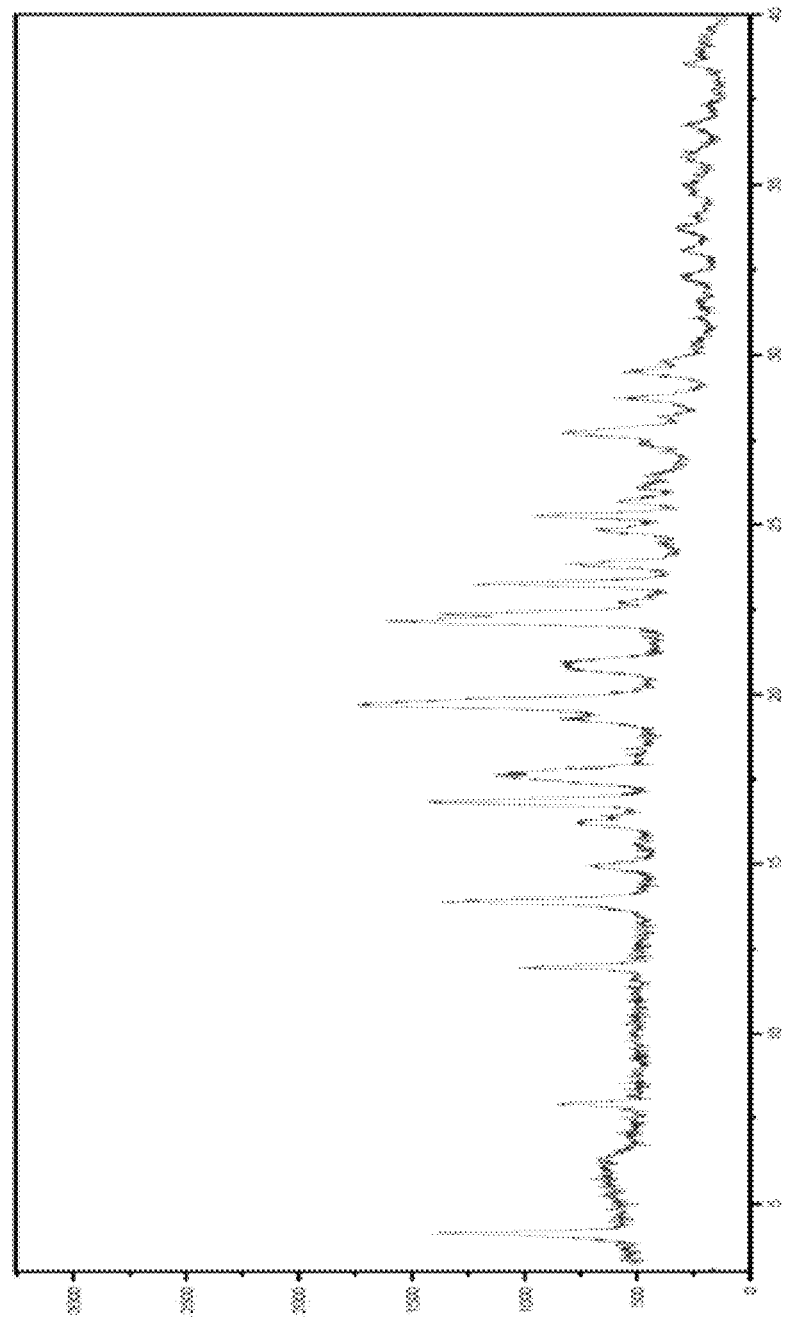
FIG. 3. XRPD of the Ketoprofen-Lysine co-crystal Form 1 collected after crystallization experiment in Dichloromethane.

Evaporation experiment of Benzyl Alcohol solution furnished Ketoprofen-Lysine co-crystal Form 1 with a yield of 80%. The evaporation of Dichloromethane solution led to the isolation of a sticky solid that was slurried in tert-Butyl methyl ether (TBME) for 24 hours; the obtained solid was obtained with a yield of 88% and was analyzed by XRPD, and the formation of Ketoprofen-Lysine co-crystal Form 1 was observed. XRPD patterns of the isolated solid are reported in FIG. 3.

2.c.iii Crystallization from Lysine Aqueous Saturated Solutions.

The experiments were performed by preparing saturated solutions of racemic Lysine (ssLYS) in water. 650 mg of racemic Lysine were dissolved in 0.5 mL of water, then the solution was filtered and added to 87 mg (0.34 mmol) of Ketoprofen. The mixture was so stirred for 24 hours at room temperature; after this time, no solid was recovered, so the solution was left to evaporate at high temperature until the formation of a sticky solid was observed. In order to get a solid suitable for XRPD analysis, the sticky solid was slurried in Isopropyl Ether (IPE) for 24 hours. After this time, the formed solid was isolated and analyzed. Ketoprofen-Lysine co-crystal Form 1 was isolated by the experiment.

The results observed after these experiments are reported in the Table 3C.

TABLE 3C

Results of crystallization experiments from Lysine saturated solution

| Solvent | Volume of ssLYS (mL) | XRPD | Yield |
|---|---|---|---|
| Water | 0.5 | KET-LYS | 80 |

2.d Preparation of Ketoprofen Lysine Salt

Figure 5:
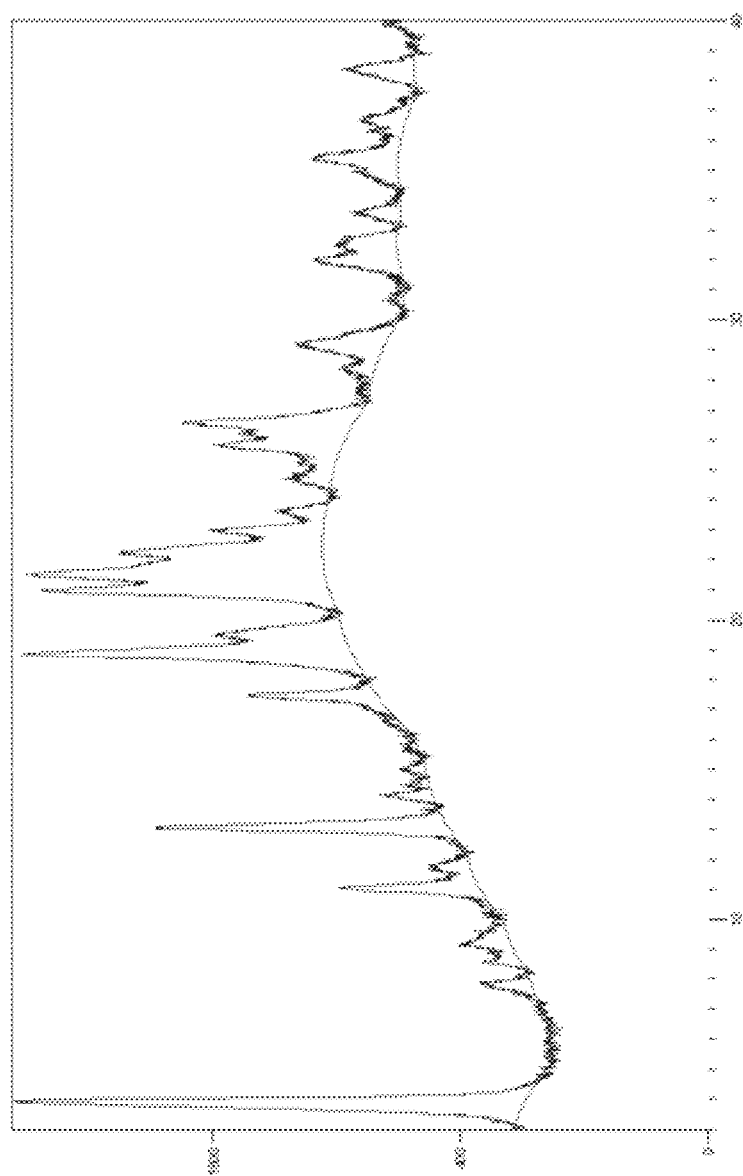
FIG. 5. XRPD pattern of comparative Ketoprofen Lysine Salt obtained according to the process described under Example 2.d.

Ketoprofen 0.76 g and racemic Lysine 0.44 g (eq. ratio 1:1) were stirred in 20 mL of methanol at 40° C. for 1 hour. Ketoprofen was dissolved while the suspended Lysine was filtered off (filter 0.45 um) directly in a Mettler Toledo Easymax 102 reactor. The solution was left under stirring for 5 minutes in the reactor, then 100 mL of ethyl acetate was added and the solution was cooled down to −5° C. without solid formation. Additional ethyl acetate (20 mL) was added through pipette in two aliquots (10 mL and 10 mL) to trigger the nucleation. The system was left under stirring until the suspension became milky. Additional 30 minutes of stirring was applied. The precipitate was then filtered and the collected sample was stored in a sealed vial at room temperature. The structure characterization XRPD (FIGS. 4, 5 and 6), FT-IR (FIGS. 10 and 12) and $^{13}$C CPMAS solid-state NMR (FIGS. 8a and 8b) of the Ketoprofen-Lysine Salt in comparison with Ketoprofen-Lysine co-crystal Form 1 are reported.

3. XRPD Analysis

The XRPD analysis has been carried out by using an instrumentation having the following characteristics:

| Instrument type: | Rigaku MiniFlex600 |
|---|---|
| Application SW: | Miniflex Guidance |
| Measurement Details | |
| Measurement type: | Single scan |
| Sample mode: | Reflection |
| Scan | |
| Scan range: | 3.000-40.000° (2θ) |
| Step size: | 0.01° (2θ) |
| Speed: | 10.0°/min (2θ) |
| Scan mode: | Continuous |
| Used wavelength | |
| Intended wavelength type: | Kα1 |
| Kα1: | 1.540598 Å |
| Kα2: | 1.544426 Å |
| Kα2/Kα1 intensity ratio: | 0.50 |
| Kα: | 1.541874 Å |
| Kβ: | 1.392250 Å |
| Instrument Details | |
| X-Ray Generator | |
| Tube output voltage: | 40 kV |
| Tube output: | 15 mA |
| High-voltage generation method: | High-frequency Cockcroft-Walton method |
| Stability: | Within ±0.05% for both the tube voltage and tube current, with reference to ±10% of input power variation. |
| X-ray tube | |
| Name: | Toshiba Analix type A-26L |
| Anode material: | Cu |
| Maximus output: | 0.60 KW |
| Focus size: | 1 × 10 mm |
| Kβ Filter | |
| Name: | Ni-filter |
| Thickness (mm): | 0.015 |
| Material: | Ni |
| Goniometer (Angle measuring device) | |
| Type: | Vertical θ/2θ |
| Goniometer radius: | 150 mm |
| Scanning axis: | θ/2θ linked |
| 2θ scanning range: | +2° to +140° |
| θ/2θ axis minimum step angle: | 0.005° (2θ) |
| Position speed: | 500°/min (2θ) |
| Scanning speed: | 0.01 to 100°/min |
| Datum angle: | 2θ = 10° |
| X-ray take-off angle: | 6° (fixed) |
| Slit | |
| DS: | 1.25° |
| IHS: | 10.0 mm |
| SS: | none (open) |
| RS: | none (open) |
| Incident side Soller slit: | 2.5° |
| Receiving side Soller slit: | 2.5° |
| Detector | |
| Name: | D/teX Ultra High-speed 1D Detector |

A sample of the co-crystal Form 1 obtained with the process of crystallization from Ketoprofen in saturated solutions of Lysine (ssLYS) in water has been analyzed by XRPD in comparison with the XRPD spectra of Ketoprofen sodium Salt (CAS Registry Number 57495-14-4).

The XRPD spectra of Ketoprofen Lysine co-crystal Form 1 according to the invention is reported in FIG. 4 and the characteristic peaks in Table 4.

The XRPD characteristic peaks of Ketoprofen sodium Salt are reported in Table 5A.

TABLE 4

XRPD Peak List of Ketoprofen Lysine co-crystal Form 1

| Pos. [°2Th.] | Height [cts] | FWHM [°2Th.] | d-spacing [Å] | Rel. Int. [%] |
|---|---|---|---|---|
| 3.8993 | 435.68 | 0.1082 | 22.66049 | 4.13 |
| 7.6804 | 319.60 | 0.1181 | 11.51101 | 3.03 |
| 11.7158 | 278.42 | 0.1378 | 7.55366 | 2.64 |
| 13.7156 | 1526.54 | 0.0600 | 6.45110 | 14.46 |
| 13.7710 | 1327.16 | 0.0480 | 6.44127 | 12.57 |
| 14.7842 | 450.23 | 0.1680 | 5.98715 | 4.26 |
| 15.7842 | 336.90 | 0.1200 | 5.61000 | 3.19 |
| 16.2898 | 4583.06 | 0.1920 | 5.43702 | 43.41 |
| 16.6144 | 1424.36 | 0.0720 | 5.33150 | 13.49 |
| 17.4718 | 7614.33 | 0.1080 | 5.07176 | 72.12 |
| 17.5514 | 10557.15 | 0.0600 | 5.04892 | 100.00 |
| 17.6104 | 9822.64 | 0.0720 | 5.03214 | 93.04 |
| 17.6712 | 7012.09 | 0.0480 | 5.02744 | 66.42 |
| 18.8701 | 217.90 | 0.1920 | 4.69896 | 2.06 |
| 19.3117 | 2354.54 | 0.1080 | 4.59250 | 22.30 |
| 19.5987 | 6977.66 | 0.0840 | 4.52590 | 66.09 |
| 19.7109 | 7735.84 | 0.1320 | 4.50038 | 73.28 |
| 20.8279 | 4063.31 | 0.1440 | 4.26147 | 38.49 |
| 22.0196 | 3815.28 | 0.1680 | 4.03348 | 36.14 |
| 22.4475 | 447.39 | 0.1680 | 3.95754 | 4.24 |
| 23.0611 | 1200.74 | 0.1080 | 3.85360 | 11.37 |
| 23.5588 | 498.90 | 0.1920 | 3.77332 | 4.73 |
| 24.6240 | 876.89 | 0.0720 | 3.61244 | 8.31 |
| 25.0036 | 1224.58 | 0.0960 | 3.55846 | 11.60 |
| 25.3727 | 529.13 | 0.0960 | 3.50752 | 5.01 |
| 26.2107 | 2232.63 | 0.1200 | 3.39724 | 21.15 |
| 26.3276 | 3781.57 | 0.0600 | 3.38242 | 35.82 |
| 26.3865 | 3564.35 | 0.0840 | 3.37501 | 33.76 |
| 26.9304 | 489.50 | 0.2640 | 3.30807 | 4.64 |
| 27.5007 | 1267.34 | 0.0960 | 3.24075 | 12.00 |
| 27.5788 | 1386.90 | 0.0720 | 3.23175 | 13.14 |
| 27.6230 | 1185.72 | 0.0720 | 3.22668 | 11.23 |
| 28.0211 | 1840.86 | 0.1080 | 3.18174 | 17.44 |
| 28.4062 | 652.51 | 0.2160 | 3.13947 | 6.18 |
| 29.3372 | 771.26 | 0.1200 | 3.04193 | 7.31 |
| 29.5194 | 1030.48 | 0.2160 | 3.02356 | 9.76 |
| 30.1298 | 113.25 | 0.4320 | 2.96368 | 1.07 |
| 30.7515 | 45.91 | 0.2880 | 2.90516 | 0.43 |
| 32.2024 | 158.44 | 0.1680 | 2.77751 | 1.50 |
| 32.8514 | 229.15 | 0.1680 | 2.72410 | 2.17 |
| 33.4488 | 163.22 | 0.1920 | 2.67680 | 1.55 |
| 34.1115 | 1217.95 | 0.0840 | 2.62630 | 11.54 |
| 34.6158 | 332.37 | 0.1680 | 2.58919 | 3.15 |
| 34.7300 | 425.65 | 0.1200 | 2.58093 | 4.03 |
| 35.4285 | 350.71 | 0.2400 | 2.53163 | 3.32 |
| 35.7591 | 668.08 | 0.2160 | 2.50898 | 6.33 |
| 36.3198 | 513.39 | 0.0960 | 2.47152 | 4.86 |
| 36.4408 | 808.53 | 0.1440 | 2.46359 | 7.66 |
| 37.1144 | 32.86 | 0.2880 | 2.42041 | 0.31 |
| 38.2975 | 350.86 | 0.1920 | 2.34832 | 3.32 |
| 39.0372 | 313.47 | 0.1920 | 2.30550 | 2.97 |

TABLE 5A

XRPD Peak List of Ketoprofen sodium Salt

| Pos. [°2Th.] | Height [cts] | FWHM [°2Th.] | d-spacing [Å] | Rel. Int. [%] |
|---|---|---|---|---|
| 5.2586 | 58.99 | 0.5510 | 16.80562 | 0.84 |
| 7.2447 | 7017.84 | 0.0886 | 12.20231 | 100.00 |
| 9.7739 | 54.29 | 0.1181 | 9.04963 | 0.77 |
| 10.7910 | 1811.29 | 0.1181 | 8.19887 | 25.81 |
| 13.3605 | 224.36 | 0.1378 | 6.62726 | 3.20 |
| 14.4207 | 221.78 | 0.1181 | 6.14233 | 3.16 |
| 15.7393 | 168.00 | 0.1181 | 5.63057 | 2.39 |
| 16.9104 | 512.57 | 0.1378 | 5.24320 | 7.30 |
| 18.1048 | 1322.27 | 0.0590 | 4.89990 | 18.84 |
| 18.7327 | 2418.71 | 0.1378 | 4.73704 | 34.47 |
| 19.1137 | 913.52 | 0.0984 | 4.64348 | 13.02 |
| 20.0517 | 819.98 | 0.0689 | 4.42833 | 11.68 |
| 21.0303 | 75.17 | 0.1968 | 4.22442 | 1.07 |
| 21.7191 | 2660.00 | 0.1476 | 4.09197 | 37.90 |
| 22.2315 | 3671.74 | 0.1378 | 3.99880 | 52.32 |
| 24.0819 | 161.01 | 0.1574 | 3.69558 | 2.29 |
| 24.4439 | 1377.06 | 0.0492 | 3.64166 | 19.62 |
| 24.8847 | 991.31 | 0.0984 | 3.57814 | 14.13 |
| 25.8156 | 33.53 | 0.2362 | 3.45120 | 0.48 |
| 26.5949 | 981.68 | 0.0689 | 3.35181 | 13.99 |
| 28.6755 | 268.69 | 0.1574 | 3.11317 | 3.83 |
| 28.9483 | 354.20 | 0.1181 | 3.08445 | 5.05 |
| 29.4014 | 284.97 | 0.1378 | 3.03794 | 4.06 |
| 29.6661 | 166.79 | 0.1574 | 3.01143 | 2.38 |
| 30.1057 | 202.66 | 0.1200 | 2.96599 | 2.89 |
| 30.2379 | 166.25 | 0.0840 | 2.96067 | 2.37 |
| 30.8737 | 141.72 | 0.1200 | 2.89394 | 2.02 |
| 31.2763 | 173.20 | 0.1680 | 2.85760 | 2.47 |
| 31.8620 | 298.97 | 0.1080 | 2.80640 | 4.26 |
| 32.4025 | 391.67 | 0.0960 | 2.76080 | 5.58 |
| 32.6399 | 229.39 | 0.1920 | 2.74127 | 3.27 |
| 33.2691 | 115.00 | 0.1440 | 2.69085 | 1.64 |
| 33.5904 | 299.42 | 0.1920 | 2.66584 | 4.27 |
| 34.9676 | 150.96 | 0.2640 | 2.56394 | 2.15 |
| 35.5019 | 152.56 | 0.2880 | 2.52656 | 2.17 |
| 36.2066 | 464.87 | 0.2880 | 2.47899 | 6.62 |
| 37.7949 | 190.00 | 0.1920 | 2.37838 | 2.71 |
| 38.2957 | 88.60 | 0.1920 | 2.34842 | 1.26 |
| 38.9966 | 81.76 | 0.1920 | 2.30781 | 1.16 |
| 39.4739 | 29.24 | 0.1920 | 2.28100 | 0.42 |

The XRPD diffractograms showed relevant signals in the region from 17 to 25° 2theta, in particular Ketoprofen sodium Salt showed the most intense peaks at 7.2447; 10.7910; 18.7327; 21.7191; 22.2315° 2theta, while Ketoprofen Lysine co-crystal Form 1 according to the invention at 16.0898; 17.4718, 17.5514; 17.8104; 17.6712; 19.5987; 19.7109° 2theta.

The XRPD spectra of Ketoprofen Lysine Salt in comparison with the XRPD spectra of Ketoprofen Lysine Co-crystal Form 1 is shown in FIG. 6 while the characteristic XRPD peaks of Ketoprofen Lysine Salt are reported in Table 5B below:

TABLE 5B

XRPD Peak List of Ketoprofen Lysine Salt

| Pos. [°2Th.] | Height [cts] | FWHM [°2Th.] | d-spacing [Å] | Rel. Int. [%] |
|---|---|---|---|---|
| 3.9325 | 2846.60 | 0.1476 | 22.46912 | 100.00 |
| 7.8614 | 122.69 | 0.1181 | 11.24637 | 4.31 |
| 8.5371 | 92.20 | 0.1181 | 10.35764 | 3.24 |
| 9.1615 | 141.64 | 0.1968 | 9.65313 | 4.98 |
| 11.0605 | 527.66 | 0.1181 | 7.99966 | 18.54 |
| 11.8024 | 131.06 | 0.2362 | 7.49843 | 4.60 |
| 13.0204 | 1516.34 | 0.0689 | 6.79958 | 53.27 |
| 14.1357 | 181.38 | 0.1968 | 6.26551 | 6.37 |
| 15.0097 | 72.85 | 0.1968 | 5.90258 | 2.56 |
| 17.4211 | 652.89 | 0.1574 | 5.09063 | 22.94 |

TABLE 5B-continued

XRPD Peak List of Ketoprofen Lysine Salt

| Pos. [°2Th.] | Height [cts] | FWHM [°2Th.] | d-spacing [Å] | Rel. Int. [%] |
|---|---|---|---|---|
| 18.8604 | 2197.33 | 0.0689 | 4.70525 | 77.19 |
| 19.4898 | 678.61 | 0.1181 | 4.55471 | 23.84 |
| 20.9970 | 1941.40 | 0.0787 | 4.23104 | 68.20 |
| 21.4845 | 2046.59 | 0.1378 | 4.13613 | 71.90 |
| 22.2596 | 1258.41 | 0.1771 | 3.99383 | 44.21 |
| 22.9984 | 616.52 | 0.0787 | 3.86717 | 21.66 |
| 23.6473 | 222.80 | 0.2362 | 3.76250 | 7.83 |
| 24.6845 | 207.27 | 0.3149 | 3.60672 | 7.28 |
| 25.8298 | 707.10 | 0.0787 | 3.44933 | 24.84 |
| 26.6005 | 977.38 | 0.0886 | 3.35111 | 34.34 |
| 28.3958 | 134.48 | 0.1574 | 3.14320 | 4.72 |
| 29.2001 | 419.42 | 0.1771 | 3.05843 | 14.73 |
| 30.7454 | 46.23 | 0.3149 | 2.90814 | 1.62 |
| 31.9837 | 376.56 | 0.1378 | 2.79832 | 13.23 |
| 32.7583 | 225.02 | 0.1574 | 2.73389 | 7.90 |
| 33.5545 | 173.12 | 0.2362 | 2.67082 | 6.08 |
| 35.3568 | 377.39 | 0.1378 | 2.53870 | 13.26 |
| 36.6756 | 185.11 | 0.2755 | 2.45038 | 6.50 |
| 38.3677 | 278.83 | 0.3149 | 2.34612 | 9.80 |

The XRPD diffractograms showed relevant signals in the region from 13 to 27° 2theta, in particular Ketoprofen Lysine Salt showed the most intense peaks at 13.0204, 17.4211, 18.8604, 19.4898, 20.9970, 21.4845 and 26.6005° 2theta, while Ketoprofen Lysine co-crystal Form 1 according to the invention at 16.2898; 17.4718, 17.5514; 17.6104; 17.6712; 19.5987; 19.7109° 2theta.

4. Solid State NMR

Solid-state NMR (ss-NMR) spectra were acquired with a Bruker Avarice II 400 Ultra Shield instrument, operating at 400.23, 100.63 and 40.56 MHz, respectively for $^1$H, $^{13}$C and $^{15}$N nuclei. Powder samples were packed into cylindrical zirconia rotors with a 4 mm o.d. and an 80 µL volume. A certain amount of sample was collected and used without further preparations to fill the rotor.

$^{13}$C CPMAS (cross polarized magic angle spinning) solid-state NMR spectra were acquired at a spinning speed of 12 kHz, using a ramp cross-polarization pulse sequence with ss-NMR spectra were acquired with a Bruker Avance II 400 Ultra Shield instrument, operating at 400.23, 100.63 and 40.56 MHz, respectively for $^1$H, $^{13}$C and $^{15}$N nuclei.

Powder samples were packed into cylindrical zirconia rotors with a 4 mm o.d. and an 80 µL volume. A certain amount of sample was collected and used without further preparations to fill the rotor.

$^{13}$C CPMAS solid-state NMR spectra were acquired at a spinning speed of 12 kHz, using a ramp cross-polarization pulse sequence with a 90° 1H pulse of 3.60 µs, a contact time of 3 ms, optimized recycle delays between 1.5 and 3.5 s, a number of scans in the range 430-640, depending on the sample.

$^{15}$N CPMAS spectra were acquired at a spinning speed of 9 kHz using a ramp cross-polarization pulse sequence with a 90° $^1$H pulse of 3.60 µs, a contact time between 1 and 4 ms, optimized recycle delays between 1.1 and 3.4 s, a number of scans in the range 14330-22770, depending on the sample.

For every spectrum, a two-pulse phase modulation (TPPM) decoupling scheme was used, with a radiofrequency field of 69.4 kHz. The $^{13}$C chemical shift scale was calibrated through the methylene signal of external standard glycine (at 43.7 ppm). The $^{15}$N chemical shift scale was calibrated through the signal of external standard glycine (at 33.4 ppm with reference to $NH_3$).

2D $^1$H-$^{13}$C on- and off-resonance (short and long-range, respectively) HETCOR spectra were measured with contact times of 0.1 and 7 ms, respectively, and FSLG t1 decoupling and TPPM t2 decoupling (rf fields of 82 kHz).

288 and 384 scans were averaged for 88 and 128 increments, respectively with 3.4 s of relaxation delay. The indirect $^1$H chemical shift scale in the HETCOR spectra was experimentally corrected by a scaling factor of ⅓ because the $^1$H chemical-shift dispersion is scaled by a factor of ⅓ during FSLG decoupling.

The $^{13}$C CPMAS solid-state NMR spectra of co-crystal Form 1 according to the invention is reported in FIG. 7.

The $^{13}$C CPMAS solid-state NMR spectra of comparative Ketoprofen Lysine Salt is reported in FIG. 8*a*.

The $^{13}$C CPMAS solid-state NMR spectra of Ketoprofen Lysine Salt in comparison with Ketoprofen Lysine Co-crystal Form 1, Ketoprofen and Lysine is reported in FIG. 8*b*.

As appears from the spectra of FIG. 8*b*, the resonances of both Ketoprofen Lysine Salt and Ketoprofen Lysine Co-crystal Form 1 differ from the characteristic signals of both the starting materials Ketoprofen and Lysine.

The main differences in the spectra of Ketoprofen Lysine Salt compared to Ketoprofen Lysine Co-crystal Form 1 are mostly in the set of interaction involving the carboxylic group of Ketoprofen and Lysine. The three signals of the carboxylic group ascribed to Ketoprofen (182.2, 181.1 and 180.0 ppm, FIG. 8*b*) of the species Ketoprofen Lysine Salt are consistent with the deprotonated nature of the carboxylic group while the signal of the un-dissociated COOH group of Ketoprofen in the Ketoprofen Lysine Co-crystal Form 1 structure falls below 180 ppm.

Table 6A and Table 6B. The assignment of the peaks in $^{13}$C CPMAS solid-state NMR of Ketoprofen Lysine co-crystal Form 1, Ketoprofen Sodium Salt and Ketoprofen Lysine Salt are reported herein below:

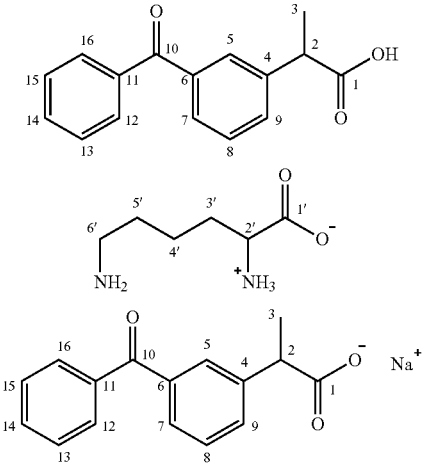

TABLE 6A

| Ketoprofen Lysine co-crystal Form 1 | | Ketoprofen Sodium Salt | |
|---|---|---|---|
| $^{13}$C δ (ppm) | C atom | $^{13}$C δ (ppm) | C atom |
| 196.1 | 10 | 200.6 | 10a |
| 177.6 | 1 | 200.1 | 10b |
| 174.5 | 1' | 181.4 | 1a |
| 147.4 | Aromatic C$_q$ (6 or 11 or 4) | 180.5 | 1b |
| 141.0 | Aromatic C$_q$ (6 or 11 or 4) | 144.2 | Aromatic C$_q$ |
| 134.8 | Aromatic C$_q$ (6 or 11 or 4) | 141.6 | Aromatic C$_q$ |
| 133.0 | Aromatic CH | 139.4 | Aromatic C$_q$ |
| 128.8 | Aromatic CH | 138.4 | Aromatic C$_q$ |
| 128.3 | Aromatic CH | 132.3 | Aromatic CH |
| 128.0 | Aromatic CH | 130.0 | Aromatic CH |
| 126.8 | Aromatic CH | 128.9 | Aromatic CH |
| 55.1 | 2' | 128.1 | Aromatic CH |
| 50.2 | 2 | 123.2 | Aromatic CH |
| 38.8 | 6' | 122.9 | Aromatic CH |
| 32.2 | 5' | 51.0 | 2a |
| 29.6 | 3' | 49.0 | 2b |
| 24.7 | 3 | 22.0 | 3a |
| 22.3 | 4' | 14.4 | 3b |

TABLE 6B $^{13}$C CPMAS solid-state NMR peak list of Ketoprofen Lysine Salt.
Ketoprofen Lysine Salt

| $^{13}$C δ (ppm) | $^{13}$C δ (ppm) |
|---|---|
| 199.8 | 127.2 |
| 197.8 | 125.9 |
| 182.2 | 564 |
| 181.1 | 55.5 |
| 180.0 | 20.8 |
| 176.6 | 49.4 |
| 175.7 | 48.2 |
| 174.3 | 38.6 |
| 144.5 | 38.2 |
| 143.8 | 32.3 |
| 142.7 | 31.7 |
| 138.2 | 26.4 |
| 134.6 | 25.7 |
| 131.8 | 22.5 |
| 129.5 | 22.0 |
| 128.6 | |

Table 6B shows the peak list of the characteristic signals of the Ketoprofen Lysine Salt. The average full width at half-maximum value (133 Hz) is consistent with a moderately crystalline phase. The carboxylic signals infer a 1:1 ratio between Ketoprofen and Lysine.

Possibly six independent molecules in the unit cell are evaluable by $^{13}$C CPMAS solid-state NMR spectra: the carboxylic signals infer the presence of 3 carboxylate moieties for both Ketoprofen and Lysine.

5. FT-IR and FT-Raman

FT-IR: The analysis was carried out using a Thermo Nicolet iS50-ATR module Spectrometer equipped with:
Smart Performer Diamond
DTGS KBr Detector
IR Source
KBr Beam splitter
Data Collection Information
Number of sample scans: 32
Number of background scans 32
Collection length: 47.29 sec
Resolution: 4,000
Levels of zero filling: 2
Number of scan points: 16672
Number of FFT points: 65536

Laser frequency: 15798, 3 cm$^{-1}$
Interferogram peak position: 8192
Apodization: N-B strong
Phase correction: Mertz
Number of background scans: 32
Background gain: 1.0
Sample gain: 6
Aperture 100
Optical velocity 0.6329

FT-Raman spectra were recorded with a Nicolet iS50 FT-IR Spectrometer. The excitation source was a Nd-YAG laser (1064 nm) in the backscattering (180°) configuration. The focused laser beam diameter was approx. 50 mm and the spectral resolution 4 cm$^{-1}$. The spectra were recorded with a laser power at the sample of approx. 100 mW.

FT-IR spectrum and FT-Raman spectrum of Ketoprofen Lysine co-crystal Form 1 according to the invention and their peak list are reported in the FIGS. 10, 11 and in Tables 7 and 8, respectively.

FT-IR and FT-Raman peak list of Ketoprofen Lysine sodium Salt are reported in Tables 9A and 10 respectively.

FT-IR spectrum and FT-Raman spectrum of Ketoprofen Lysine Salt and the peak list are reported in the FIGS. 12 and 11 and Table 9B respectively.

TABLE 7

Peak list of the FT-IR spectrum of
Ketoprofen Lysine co-crystal Form 1
Peak List

| Position | Intensity |
|---|---|
| 412 | 70.137 |
| 441 | 77.258 |
| 448 | 80.669 |
| 486 | 45.930 |
| 549 | 73.524 |
| 620 | 54.809 |
| 651 | 69.299 |
| 666 | 65.871 |
| 687 | 56.786 |
| 696 | 62.440 |
| 708 | 46.485 |
| 715 | 43.933 |
| 731 | 84.532 |
| 784 | 72.134 |
| 797 | 70.060 |
| 815 | 76.999 |
| 825 | 77.325 |
| 832 | 81.431 |
| 852 | 76.991 |
| 872 | 72.342 |
| 882 | 58.800 |
| 895 | 86.893 |
| 935 | 93.097 |
| 971 | 73.456 |
| 1003 | 77.074 |
| 1022 | 78.405 |
| 1043 | 89.951 |
| 1070 | 80.462 |
| 1083 | 82.338 |
| 1101 | 85.567 |
| 1138 | 68.451 |
| 1158 | 87.896 |
| 1175 | 74.914 |
| 1197 | 73.233 |
| 1223 | 79.989 |
| 1247 | 59.043 |
| 1273 | 41.449 |
| 1286 | 42.036 |
| 1315 | 50.763 |
| 1331 | 69.556 |
| 1352 | 51.614 |
| 1364 | 66.337 |
| 1398 | 37.374 |

TABLE 7-continued

Peak list of the FT-IR spectrum of
Ketoprofen Lysine co-crystal Form 1
Peak List

| Position | Intensity |
|---|---|
| 1431 | 73.698 |
| 1448 | 64.543 |
| 1455 | 58.033 |
| 1484 | 60.127 |
| 1542 | 51.389 |
| 1577 | 39.398 |
| 1586 | 39.616 |
| 1631 | 54.419 |
| 1665 | 52.612 |
| 2601 | 78.326 |
| 2679 | 77.361 |
| 2817 | 73.411 |
| 2858 | 72.192 |
| 2919 | 73.338 |
| 2962 | 74.418 |
| 3055 | 85.101 |
| 3170 | 89.842 |

TABLE 8

Peak list of the FT-Raman spectrum of
Ketoprofen Lysine co-crystal Form 1
Peak list:

| Position | Intensity |
|---|---|
| 405 | 4.079 |
| 433 | 4.149 |
| 489 | 8.298 |
| 552 | 3.812 |
| 619 | 12.034 |
| 652 | 5.582 |
| 699 | 12.319 |
| 709 | 17.337 |
| 850 | 7.016 |
| 874 | 9.894 |
| 934 | 5.214 |
| 972 | 8.158 |
| 1002 | 78.866 |
| 1028 | 12.588 |
| 1043 | 5.890 |
| 1076 | 9.388 |
| 1137 | 14.158 |
| 1169 | 13.919 |
| 1182 | 13.473 |
| 1193 | 23.310 |
| 1247 | 7.418 |
| 1286 | 10.733 |
| 1314 | 11.948 |
| 1338 | 8.344 |
| 1405 | 8.461 |
| 1440 | 9.612 |
| 1462 | 8.437 |
| 1485 | 3.668 |
| 1545 | 3.946 |
| 1596 | 60.158 |
| 1664 | 53.818 |
| 2563 | 3.628 |
| 2628 | 4.547 |
| 2673 | 4.168 |
| 2713 | 5.167 |
| 2737 | 5.915 |
| 2765 | 6.224 |
| 2866 | 19.637 |
| 2922 | 53.412 |
| 2967 | 31.934 |
| 3027 | 14.424 |
| 3064 | 67.759 |
| 3128 | 5.228 |

TABLE 8-continued

Peak list of the FT-Raman spectrum of
Ketoprofen Lysine co-crystal Form 1
Peak list:

| Position | Intensity |
| --- | --- |
| 3155 | 5.872 |
| 3200 | 4.431 |

TABLE 9A

Peak list of the FT-IR spectrum of
Ketoprofen sodium Salt

| Position (cm$^{-1}$) | Intensity |
| --- | --- |
| 429 | 47.958 |
| 450 | 67.736 |
| 485 | 62.079 |
| 581 | 59.026 |
| 608 | 49.504 |
| 645 | 20.703 |
| 674 | 45.042 |
| 688 | 21.598 |
| 701 | 20.966 |
| 719 | 25.875 |
| 784 | 45.878 |
| 805 | 72.985 |
| 822 | 67.726 |
| 841 | 64.615 |
| 884 | 42.140 |
| 932 | 81.401 |
| 953 | 59.710 |
| 999 | 81.442 |
| 1020 | 82.601 |
| 1030 | 85.312 |
| 1068 | 70.099 |
| 1104 | 84.982 |
| 1141 | 81.367 |
| 1175 | 65.123 |
| 1197 | 72.826 |
| 1243 | 44.516 |
| 1258 | 49.940 |
| 1276 | 36.862 |
| 1296 | 43.082 |
| 1321 | 34.820 |
| 1363 | 50.753 |
| 1397 | 26.410 |
| 1445 | 58.051 |
| 1462 | 73.435 |
| 1477 | 84.257 |
| 1570 | 16.521 |
| 1582 | 19.151 |
| 1656 | 37.290 |
| 2874 | 96.175 |
| 2912 | 91.001 |
| 2931 | 92.937 |
| 2966 | 87.542 |
| 3062 | 93.322 |
| 3386 | 91.434 |

TABLE 9B

Peak list of the FT-IR spectrum of
Ketoprofen Lysine Salt

| Position (cm$^{-1}$) | Intensity |
| --- | --- |
| 414 | 51.203 |
| 437 | 69.203 |
| 463 | 76.990 |
| 475 | 76.368 |
| 518 | 63.818 |
| 539 | 60.253 |
| 621 | 69.700 |
| 645 | 61.177 |
| 675 | 72.596 |
| 689 | 66.858 |
| 706 | 55.062 |
| 713 | 56.968 |
| 756 | 82.432 |
| 779 | 73.315 |
| 802 | 80.054 |
| 821 | 87.571 |
| 831 | 88.245 |
| 871 | 69.950 |
| 911 | 88.295 |
| 929 | 90.674 |
| 958 | 84.976 |
| 967 | 88.368 |
| 1007 | 80.471 |
| 1072 | 84.876 |
| 1138 | 77.764 |
| 1160 | 79.502 |
| 1179 | 81.151 |
| 1201 | 81.656 |
| 1248 | 65.816 |
| 1281 | 53.933 |
| 1320 | 58.117 |
| 1358 | 59.706 |
| 1393 | 53.834 |
| 1420 | 69.095 |
| 1448 | 68.893 |
| 1479 | 72.920 |
| 1532 | 44.203 |
| 1538 | 43.543 |
| 1557 | 42.899 |
| 1615 | 73.015 |
| 1652 | 65.459 |
| 2050 | 95.210 |
| 2089 | 95.059 |
| 2112 | 94.226 |
| 2324 | 93.704 |
| 2650 | 84.309 |
| 2879 | 75.764 |
| 2942 | 72.790 |
| 3420 | 95.023 |

TABLE 10

Peak list of the FT-Raman spectrum of
Ketoprofen sodium Salt

| Position (cm$^{-1}$) | Intensity |
| --- | --- |
| 102 | 1160.009 |
| 165 | 474.578 |
| 224 | 262.371 |
| 291 | 80.737 |
| 405 | 38.647 |
| 431 | 39.619 |
| 615 | 65.766 |
| 701 | 114.002 |
| 722 | 46.145 |
| 786 | 37.023 |
| 885 | 71.029 |
| 1001 | 574.704 |
| 1026 | 140.789 |
| 1140 | 77.492 |
| 1160 | 89.545 |
| 1196 | 219.581 |
| 1246 | 59.734 |
| 1292 | 39.549 |
| 1317 | 43.223 |
| 1407 | 54.635 |
| 1459 | 48.167 |
| 1597 | 535.213 |

TABLE 10-continued

Peak list of the FT-Raman spectrum of
Ketoprofen sodium Salt

| Position (cm$^{-1}$) | Intensity |
|---|---|
| 1664 | 392.191 |
| 2874 | 54.582 |
| 2910 | 121.051 |
| 2932 | 111.658 |
| 2965 | 109.112 |
| 3025 | 63.116 |
| 3061 | 362.268 |

6. DSC Analysis

The analysis was carried out using a DSC Mettler Toledo DSC1.

The samples of Ketoprofen Lysine co-crystal Form 1 and of Ketoprofen Lysine Salt were weighed in an aluminum pan hermetically sealed with an aluminum cover. The analysis was performed heating the sample from 25° C. to 320° C. at 10 K/min.

| Temperature data | |
|---|---|
| Temperature range | 25° C. to 320° C. |
| Temperature accuracy | ±0.2 K. |
| Temperature precision | ±0.02 K. |
| Heating rate | 10 K./min |
| Cooling time | 5 min (100° C. . . . 0° C.) |

| Calorimetric Data | |
|---|---|
| Sensor type | FRS5 |
| Sensor material | Ceramic |
| Number of thermocouples | 56 |
| Signal time constant | 1.8 s |
| Indium peak (height to width) | 17 |
| TAWN resolution | 0.12 |
| Sensitivity | 11.9 |
| Resolution | 0.04 µW |
| Digital resolution | 16.8 million points |

DSC thermogram of Ketoprofen Lysine co-crystal Form 1 is reported in FIG. 13. The DSC thermogram of Ketoprofen Lysine co-crystal Form 1 shows an endothermic peak at onset temperature 164.14° C.

DSC thermogram of Ketoprofen Lysine Salt is reported in FIG. 14.

The DSC thermogram of Ketoprofen Lysine Salt shows:

A first endothermic peak (54.67 J/g) onset 100.53° C., peak 110.92° C., endset 118.35° C.

Above 120° C. multiple partially overlapped endothermic peaks due to degradation steps.

7. Dissolution Rate

The dissolution rate of Ketoprofen Sodium Salt and Ketoprofen Lysine co-crystal Form 1 have been analyzed.
Method Product (25 mg powder sample) were tested in a USP39 Apparatus 2 (Distek Dissolution System 2100B) in 250 ml USP buffer pH 1.2, at 37° C. and 100 rpm paddle rotation speed.

The amount of solid dissolved at each time point was determined spectrophotometrically at 260 nm.

The dissolution profiles (mean of 2 replicates) of Ketoprofen Lysine co-crystal Form 1 according to the invention and Ketoprofen Sodium Salt are shown in FIG. 15.

Dissolution Rate Ketoprofen Lysine Co-Crystal Form 1 (Formulate)
Method

The dissolution test was performed in a Sotax AT7-smart dissolution apparatus equipped with the paddle arrangement according to 2018 edition of European Pharmacopoeia. The quantitative assay was determined by HPLC against external standard.

The dissolution was performed on Ketoprofen Lysine co-crystal Form 1 as a granulate with the following composition: Ketoprofen Lysine co-crystal Form 1 (Active Ingredient). Excipients: Mannitol, Povidone, Anhydrous colloidal silica, Sodium chloride, Sodium saccharin, Ammonium glycyrrhizinate, Mint flavor.

The dissolution medium was prepared dissolving 29.2 g of NaCl in about 3 liters of water, then 70.6 ml of HCl were added and diluted to 10 liters with water. The pH was adjusted to 1.2.

Approximately 76 mg of product were placed in each of the 6 vessels containing 1000 ml of the dissolution medium. At each sampling time 5 ml aliquot was withdrawn and filtered through 1.5 mm Wathman 934-AH filters. The filtered solution was injected in HPLC.
Instrumental Condition:

Apparatus: dissolution apparatus Sotax AT7-smart.
Dissolution volume: 1000 ml.
Temperature: 37±0.5° C.
Rotation speed: 100 rpm.
Sampling time: 5, 10, 15, 20, 30, 45, 60.

Solubility

The solubility of Ketoprofen Lysine co-crystal Form 1 at different pH is shown in Table 11 below. Ketoprofen Lysine co-crystal Form 1 has a solubility of 280 mg/mL at pH 6.8.

TABLE 11

Solubility of Ketoprofen Lysine
co-crystal Form 1 at different pH

| pH | Solubility (mg/mL) |
|---|---|
| 1.0 | 0.33 |
| 4.6 | 1.82 |
| 6.8 | 280.2 |

8. Other Tests
Loss on Drying Assay

The loss on drying of Ketoprofen Sodium Salt and Ketoprofen Lysine co-crystal Form 1 have been assessed in long term and accelerated conditions according to the 2018 of European Pharmacopoeia. The results are shown in the following Tables 12A and 12B.

TABLE 12A

| | | Long term conditions (25° C./60% RH) | | | | | |
|---|---|---|---|---|---|---|---|
| | | Storage (months) | | | | | |
| Test Appearance | Limits White powder | 0 White powder | 3 White powder | 6 White powder | 9 White powder | 12 White powder | |
| Ketoprofen Sodium Salt | | | | | | | |
| Loss on drying (%) | ≤5.0% | 1.27 | 3.25 | 5.53 | 5.78 | 6.35 | |
| Ketoprofen Lysine co-crystal Form 1 (invention) | | | | | | | |
| Loss on drying (%) | ≤5.0% | 0.13 | 0.31 | 0.31 | 0.32 | 0.29 | |

TABLE 12B

| | | Accelerated conditions (40 °C./75% RH) | | | | | |
|---|---|---|---|---|---|---|---|
| | | Storage (months) | | | | | |
| Test Appearance | Limits White powder | 0 White powder | 1 White powder | 2 White powder | 3 White powder | 6 White powder | 12 White powder |
| Ketoprofen Sodium Salt | | | | | | | |
| Loss on drying (%) | ≤5.0% | 1.28 | 1.68 | 2.05 | 3.95 | 6.17 | 7.27 |
| Ketoprofen Lysine co-crystal Form 1 (invention) | | | | | | | |
| Loss on drying (%) | ≤5.0% | 0.13 | 0.34 | 0.27 | 0.49 | 0.48 | 0.50 |

Particle Size Distribution

Ketoprofen Lysine Co-crystal Form 1 and Ketoprofen Lysine Salt were analysed by Mastersizer laser diffraction. Particle size analysis is related to the rheological behaviour of the powder and to the dissolution rate of the product. A significant variation of the particle size between Ketoprofen Lysine Co-crystal Form 1 and Ketoprofen Lysine Salt was observed, as reported in the following Table 13:

TABLE 13

Comparison between the PSD of Ketoprofen Lysine
Co-crystal Form 1 and Ketoprofen Lysine Salt.

| PSD | Ketoprofen Lysine Co-crystal Form 1 | Ketoprofen Lysine Salt |
|---|---|---|
| D10 (μm) | 4.4 | 84 |
| D50 (μm) | 82.0 | 131 |
| D90 (μm) | 192.3 | 348 |

Crystallinity

As demonstrated by the XRPD analysis, the Ketoprofen Lysine co-crystal Form 1 has a crystallinity significantly higher than the Ketoprofen Lysine Salt where the presence of amorphous phase is evident (FIG. 17).

The lower particle size diameter of the present Ketoprofen Lysine co-crystal Form 1 combined with higher crystallinity can provide for many advantages in comparison with the previous Ketoprofen Lysine Salt, in fact, particle size distribution plays an important part in the production process (quality control) and in the development of suitable manufacturing methods. Smaller final mean particle sizes can improve content uniformity, solubility, dissolution, absorption rates and bioavailability.

A further advantage of the present Ketoprofen Lysine Co-Crystal Form 1 compared with the previous Ketoprofen Lysine Salt is that it can be obtained directly from the crystallization step in a lower particle size, thus minimizing or even avoiding downstream micronization of the powder in order to get the desired particle size diameter, with a potential reduction of process steps, time and, in the end, manufacturing costs.

Finally, the superior crystallinity of the present Ketoprofen Lysine co-crystal Form 1 compared with Ketoprofen salts such as Ketoprofen Sodium or Lysine Salt is advantageous in terms of increased stability of the product.

The invention claimed is:

1. A co-crystal of Ketoprofen Lysine Form 1 characterized by having an X-ray diffraction pattern with characteristic peaks at 16.3; 17.5; 17.6; 17.7; 19.6; 19.7° 2theta±0.20 degrees.

2. The co-crystal according to claim 1, characterized by having a X ray the following X-ray diffraction pattern characteristic peaks: 43.8993; 7.6804; 11.7158; 13.7156; 13.7710; 14.7842; 15.7842; 16.2898; 16.6144; 17.4718; 17.5514; 17.6104; 17.6712; 18.8701; 19.3117; 19.5987; 19.7109; 20.8279; 22.0196; 22.4475; 23.0611; 23.5588; 24.6240; 25.0036; 25.3727; 26.2107:26.3276:26.3865; 26.9304; 27.5007:27.5788; 27.6230; 28.0211; 28.4062; 29.3372; 29.5194; 30.1298; 30.7515; 32.2024; 32.8514; 33.4488; 34.1115; 34.6158; 34.7300; 35.4285; 35.7591; 36.3198; 36.4408; 37.1144; 38.2975; 39.0372 2theta±0.20 degrees.

3. The co-crystal according to claim 1, wherein the molecular ratio between Ketoprofen and Lysine is 1:1.

4. The co-crystal according to claim 1, wherein said co-crystal is selected from the group consisting of: (R)-2-(3-benzoylphenyl)-propionic acid D-Lysine, (R)-2-(3-benzoylphenyl)-propionic acid L-Lysine, (S)-2-(3-benzoylphenyl)-propionic acid D-Lysine and(S)-2-(3-benzoylphenyl)-propionic acid L-Lysine.

5. The co-crystal according to claim 1, having a particle size distribution with a D90 lower than 300 μm.

6. A pharmaceutical composition comprising the co-crystal according to claim 1 and one or more physiologically acceptable excipients.

7. The pharmaceutical composition according to claim 6, wherein said one or more excipients are selected from the group consisting of: povidone, colloidal silica, hydroxypropylmethylcellulose, copolymer of butyl methacrylate, dimethylaminoethyl methacrylate and methyl methacrylate, sodium dodecyl sulfate, stearic acid, magnesium stearate, aspartame, mannitol, xylitol, talc, and flavors.

8. The pharmaceutical composition according to claim 6, wherein said pharmaceutical composition is in solid granulate form.

9. A pharmaceutical composition comprising the co-crystal of Ketoprofen Lysine Form 1 according to claim 1 in combination with one or more pharmaceutically active agents.

10. A method of treating a condition selected from pain and inflammation diseases in a subject in need thereof, comprising administering an effective amount of the co-crystal of Ketoprofen Lysine Form 1 according to claim 1, wherein the co-crystal is administered alone or in combination with one or more physiologically acceptable excipients.

11. The method according to claim 10, wherein the pain is selected from the group consisting of: acute pain, headache, toothache, menstrual pain, muscle pain, and osteoarticular pain.

12. The method according to claim 10, wherein the inflammation disease is rheumatitis disease.

13. The co-crystal according to claim 5, having a particle size distribution with a D90 lower than 250 μm.

14. The co-crystal according to claim 5, having a particle size distribution with a D90 lower than 200 μm.

* * * * *

UNITED STATES PATENT AND TRADEMARK OFFICE
CERTIFICATE OF CORRECTION

PATENT NO. : 12,285,396 B2
APPLICATION NO. : 17/416627
DATED : April 29, 2025
INVENTOR(S) : Andrea Aramini, Gianluca Bianchini and Samuele Lillini It is certified that error appears in the above-identified patent and that said Letters Patent is hereby corrected as shown below:

In the Claims

Claim 2, Column 26, Line 12: "43.8993" should read -- 3.8993 --.

Claim 2, Column 26, Line 15: "26.2107:26.3276:26.3865" should read -- 26.2107; 26.3276; 26.3865 --.

Claim 2, Column 26, Line 16: "27.5007:27.5788" should read -- 27.5007; 27.5788 --.

Signed and Sealed this
Twenty-seventh Day of May, 2025

Coke Morgan Stewart
*Acting Director of the United States Patent and Trademark Office*